US010642956B2

(12) United States Patent
Matsuki

(10) Patent No.: US 10,642,956 B2
(45) Date of Patent: May 5, 2020

(54) MEDICAL REPORT GENERATION APPARATUS, METHOD FOR CONTROLLING MEDICAL REPORT GENERATION APPARATUS, MEDICAL IMAGE BROWSING APPARATUS, METHOD FOR CONTROLLING MEDICAL IMAGE BROWSING APPARATUS, MEDICAL REPORT GENERATION SYSTEM, AND NON-TRANSITORY COMPUTER READABLE MEDIUM

(71) Applicant: CANON KABUSHIKI KAISHA, Tokyo (JP)

(72) Inventor: Naoki Matsuki, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/481,231

(22) Filed: Apr. 6, 2017

(65) Prior Publication Data

US 2017/0300664 A1 Oct. 19, 2017

(30) Foreign Application Priority Data

Apr. 13, 2016 (JP) ................................ 2016-080539

(51) Int. Cl.
*G16H 15/00* (2018.01)
*G06F 19/00* (2018.01)

(52) U.S. Cl.
CPC ........... *G06F 19/321* (2013.01); *G16H 15/00* (2018.01)

(58) Field of Classification Search
CPC ............. G06F 19/321; G06F 17/30277; G06F 17/3028; G06F 17/21; G06F 17/30247; G06F 17/30268; G06F 17/30554; G16H 15/00
See application file for complete search history.

(56) References Cited

U.S. PATENT DOCUMENTS

| 2006/0274928 A1* | 12/2006 | Collins ..................... A61B 6/00 382/132 |
| 2009/0087049 A1 | 4/2009 | Takahashi |
| 2012/0183188 A1* | 7/2012 | Moriya ................. G06F 19/321 382/128 |
| 2013/0290826 A1 | 10/2013 | Niwa |
| 2014/0316770 A1* | 10/2014 | Sevenster ............... G06F 17/21 704/9 |

(Continued)

FOREIGN PATENT DOCUMENTS

| JP | 2009-086765 A | 4/2009 |
| JP | 2013-132514 A | 7/2013 |
| JP | 2013-152699 A | 8/2013 |

*Primary Examiner* — Wilson W Tsui
(74) *Attorney, Agent, or Firm* — Canon USA, Inc. IP Division

(57) ABSTRACT

A medical report generation apparatus which generates a medical report including region information of a target region specified in a medical image includes one or more processors, an obtaining unit configured to obtain at least a representative image based on the medical image and group information indicating a group of the region information, and a display unit configured to update and display the representative image of the medical report such that the group is distinguishable in accordance with the group information obtained by the obtaining unit.

14 Claims, 18 Drawing Sheets

(56) References Cited

U.S. PATENT DOCUMENTS

| | | | | |
|---|---|---|---|---|
| 2015/0317434 A1* | 11/2015 | Kondo | ..................... | A61B 5/00 |
| | | | | 705/3 |
| 2016/0048987 A1* | 2/2016 | Sevenster | ............... | G06T 11/60 |
| | | | | 715/232 |
| 2016/0055394 A1* | 2/2016 | Kanada | ................. | G06T 7/0014 |
| | | | | 382/128 |

\* cited by examiner

FIG. 3A

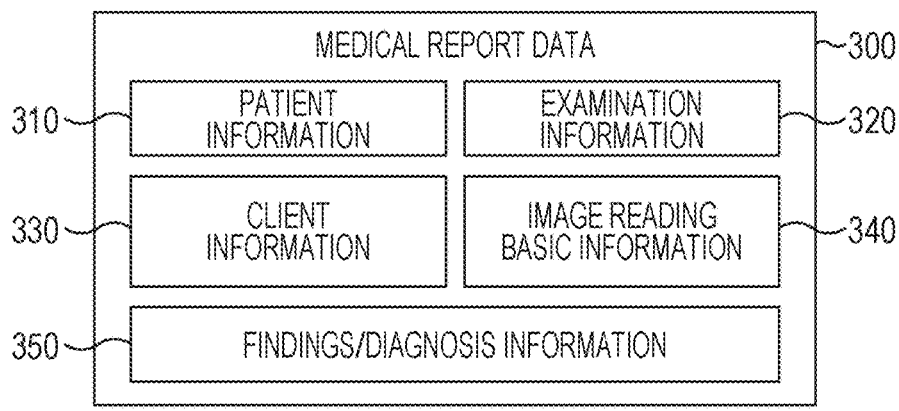

FIG. 3B

| ITEM ID | TYPE | DETAIL | ASSOCIATED ITEM ID |
|---|---|---|---|
| 1 | REGION | REGION ID: 1 | 2 |
| 2 | FINDINGS | THE LEFT KIDNEY HAS BEEN REMOVED. NO LOCAL RECURRENCE IS FOUND. | 1, 3 |
| 3 | DIAGNOSIS | POSTOPERATIVE COURSE OF LEFT KIDNEY CANCER. A DEFINITE RECURRENCE IS NOT SPECIFIED. | 2 |
| 4 | REGION | REGION ID: 2 | 5 |
| 5 | FINDINGS | A SOFT TISSUE MASS WITH OSTEOLYSIS IS FOUND IN THE L1 VERTEBRAL BODY. NO SIGNIFICANT CHANGE FROM THE PREVIOUS SCAN. | 4, 6 |
| 6 | DIAGNOSIS | LUMBAR SPINE METASTASIS DOES NOT TEND TO BE INCREASED. | 5 |
| ⋮ | ⋮ | ⋮ | ⋮ |

FIG. 6

| REGION ID | IMAGE ADDRESS | POSITIONAL INFORMATION | IMAGE PROCESSING INFORMATION | REGION RENDERING INFORMATION | REPRESENTATIVE IMAGE | GROUP ID |
|---|---|---|---|---|---|---|
| 1 | \aa\aa\a a\1.dcm | x="0.01", y="0.01", w="0.01", h="0.01" | WL: 630 *1<br>WW: 413 *2 | SHAPE: ELLIPSE<br>LINE COLOR: RED<br>DOTTED LINE: ON | IMAGE | 1 |
| 2 | \aa\aa\b b\1.dcm | x="0.2", y="0.16", w="0.08", h="0.06" | WL: 743<br>WW: 373 | SHAPE: ELLIPSE<br>LINE COLOR: RED<br>DOTTED LINE: OFF | IMAGE | 1 |
| 3 | \aa\aa\b b\1.dcm | x="0.1", y="0.6", w="0.1", h="0.06" | WL: 880<br>WW: 442 | SHAPE: RECT<br>LINE COLOR: RED<br>DOTTED LINE: OFF | IMAGE | 1 |
| 4 | \aa\aa\b b\4.dcm | x="0.8", y="0.7", w="0.04", h="0.05" | WL: 795<br>WW: 392 | SHAPE: RECT<br>LINE COLOR: RED<br>DOTTED LINE: OFF | IMAGE | 2 |
| 5 | \aa\aa\a a\3.dcm | x="0.3", y="0.4", w="0.12", h="0.04" | WL: 620<br>WW: 360 | SHAPE: RECT<br>LINE COLOR: RED<br>DOTTED LINE: OFF | IMAGE | 3 |
| ... | ... | | | | | |

*1 WL: WINDOW LEVEL
*2 WW: WINDOW WIDTH

FIG. 9B

| EXAMINATION DATE | PATIENT NAME | AGE/GENDER | PHOTOGRAPHING DEVICE | CLIENT DOCTOR | STATUS | IMAGE READING DOCTOR |
|---|---|---|---|---|---|---|
| 6/2/2014 | HANAKO SATO | 78/F | CT | ICHIRO TANAKA | NOT PHOTOGRAPHED | |
| 6/2/2014 | TARO TAMACHI | 56/M | CT/MR | JIRO UENO | FINDINGS/DIAGNOSIS IS BEING INPUT | JIRO SAKAMOTO |
| 6/2/2014 | TARO SUZUKI | 36/M | CT | TARO SHINAGAWA | INPUT OF QUESTIONS IS ENDED | SABURO SAITO |
| 6/2/2014 | TOSHI SAKAMOTO | 62/F | CT | GORO HAMAMATSU | INPUT OF FINDINGS/DIAGNOSIS IS ENDED | SHIRO SUZUKI |
| 6/1/2014 | JIRO KAMATA | 65/M | CT | TARO SHINAGAWA | INPUT OF REPLY IS ENDED | JIRO SAKAMOTO |
| 6/1/2014 | MARUKO SHIMO | 32/F | MR | JIRO UENO | INPUT OF FINDINGS/DIAGNOSIS IS ENDED | SABURO SAITO |
| 6/1/2014 | JIN KAWASAKI | 26/M | CT | ICHIRO TANAKA | INPUT OF FINDINGS/DIAGNOSIS IS ENDED | SABURO SAITO |

- ☑ PATIENT NAME  ☐ PHOTOGRAPHING DEVICE
- ☐ EXAMINATION DATE [ ] TO [ ]  ☐ QUESTION/REPLY

SEARCH

ENTER

| PATIENT INFORMATION | | | |
|---|---|---|---|
| ID | AA123456789 | GENDER | MALE |
| NAME | TARO SHIMOMARU | AGE | 79 |
| BIRTH DATE | 3/4/1930 | MEDICAL HISTORY | |

| PATIENT INFORMATION | | | |
|---|---|---|---|
| EXAMINATION DATE | 8/23/2009 | BRANCH OF MEDICINE | DIGESTIVE SURGERY |
| EXAMINATION PORTION | BREAST | CLINICIAN | JIRO KOSUGI |
| PHOTOGRAPHING DEVICE | CT NO CONTRAST AGENT | CONTENT OF REQUEST | SUSPICION OF LUNG CANCER |

FINDINGS/DIAGNOSIS

REGION INFORMATION — 1411, 1412, 1413

FINDINGS
- CALCIFIED TUBER IS FOUND IN LEFT LUNG. (1421)
- CYST IS FOUND IN RIGHT LUNG.

DIAGNOSIS
- MULTIPLE PULMONARY METASTASIS OF BOWEL CANCER IS SUSPECTED. (1422)

COMPLETION OF INPUT

1420

MEDICAL REPORT GENERATION APPARATUS, METHOD FOR CONTROLLING MEDICAL REPORT GENERATION APPARATUS, MEDICAL IMAGE BROWSING APPARATUS, METHOD FOR CONTROLLING MEDICAL IMAGE BROWSING APPARATUS, MEDICAL REPORT GENERATION SYSTEM, AND NON-TRANSITORY COMPUTER READABLE MEDIUM

BACKGROUND

Field of Art

The present disclosure relates to a medical report generation apparatus for generating a medical report, a method for controlling the medical report generation apparatus, a medical image browsing apparatus for browsing a medical image, a method for controlling the medical image browsing apparatus, a medical report generation system including the medical report generation apparatus and the medical image browsing apparatus, and a non-transitory computer readable medium.

Description of the Related Art

In recent years, an amount of information on medical image data obtained in one examination is increased since performance of medical image photographing apparatuses is improved. Therefore, content of description in a medical report, such as an image reading report, is complicated, and a burden of interpretation of the medical report for a client of examination is considerably increased.

When the medical report is interpreted, characteristics of a lesion which is mentioned in findings and diagnosis which is derived from the findings are required to be properly recognized. An image of a lesion found in image reading is saved in a medical report as a key image (which is referred to as a "representative image" hereinafter). The client may properly recognize characteristics of the lesion with reference to the representative image.

Examples of the lesion include a lesion to be collectively coped with in diagnosis, such as a multiple pulmonary metastasis of a bowel cancer. A method for collectively coping with such a lesion is described in Japanese Patent Laid-Open No. 2013-152699. Specifically, in Japanese Patent Laid-Open No. 2013-152699, a plurality of annotations displayed in an image viewer are grouped in accordance with a user's instruction.

SUMMARY

According to an embodiment, a medical report generation apparatus which generates a medical report including region information of a target region specified in a medical image includes one or more processors, an obtaining unit configured to obtain at least a representative image based on the medical image and group information indicating a group of the region information, and a display unit configured to update and display the representative image of the medical report such that the group is distinguishable in accordance with the group information obtained by the obtaining unit.

According to another embodiment, a medical image browsing apparatus for browsing a medical image includes one or more processors, a browsing unit configured to display the medical image in a browsing available manner, and a generation unit configured to generate at least a representative image based on the medical image and group information indicating a group of region information corresponding to a target region specified in the medical image.

Further features of the invention will become apparent from the following description of exemplary embodiments with reference to the attached drawings.

BRIEF DESCRIPTION OF THE DRAWINGS

FIGS. 3A and 3B are diagrams illustrating data configurations of a medical report generated by the medical report generation apparatus according to the first embodiment.

FIG. 6 is a diagram illustrating region information stored in a region information storage unit of FIG. 5.

FIGS. 9A and 9B are diagrams illustrating GUI screens used in the medical report generation process performed by the medical report generation system according to the first embodiment.

FIGS. 10A and 10B are diagrams illustrating GUI screens used in the medical report generation process performed by the medical report generation system according to the first embodiment.

FIGS. 14A and 14B are diagrams illustrating GUI screens displayed in a medical report generation apparatus according to the second embodiment.

DESCRIPTION OF THE EMBODIMENTS

In the method described in "BACKGROUND", information on a group is displayed only in an image viewer. Therefore, an associated lesion is not recognized only when a medical report is viewed, and therefore, a user bothers to activate the image viewer to check the information on the group.

Specifically, in the related art, it is difficult to recognize the plurality of associated lesions only from the medical report.

The disclosed technique is to provide a system which enables recognition of a plurality of associated lesions only from a medical report.

Hereinafter, embodiments will be described with reference to the accompanying drawings.

First Embodiment

A first embodiment will now be described.

Schematic Configuration of Medical Report Generation System

Figure 1:
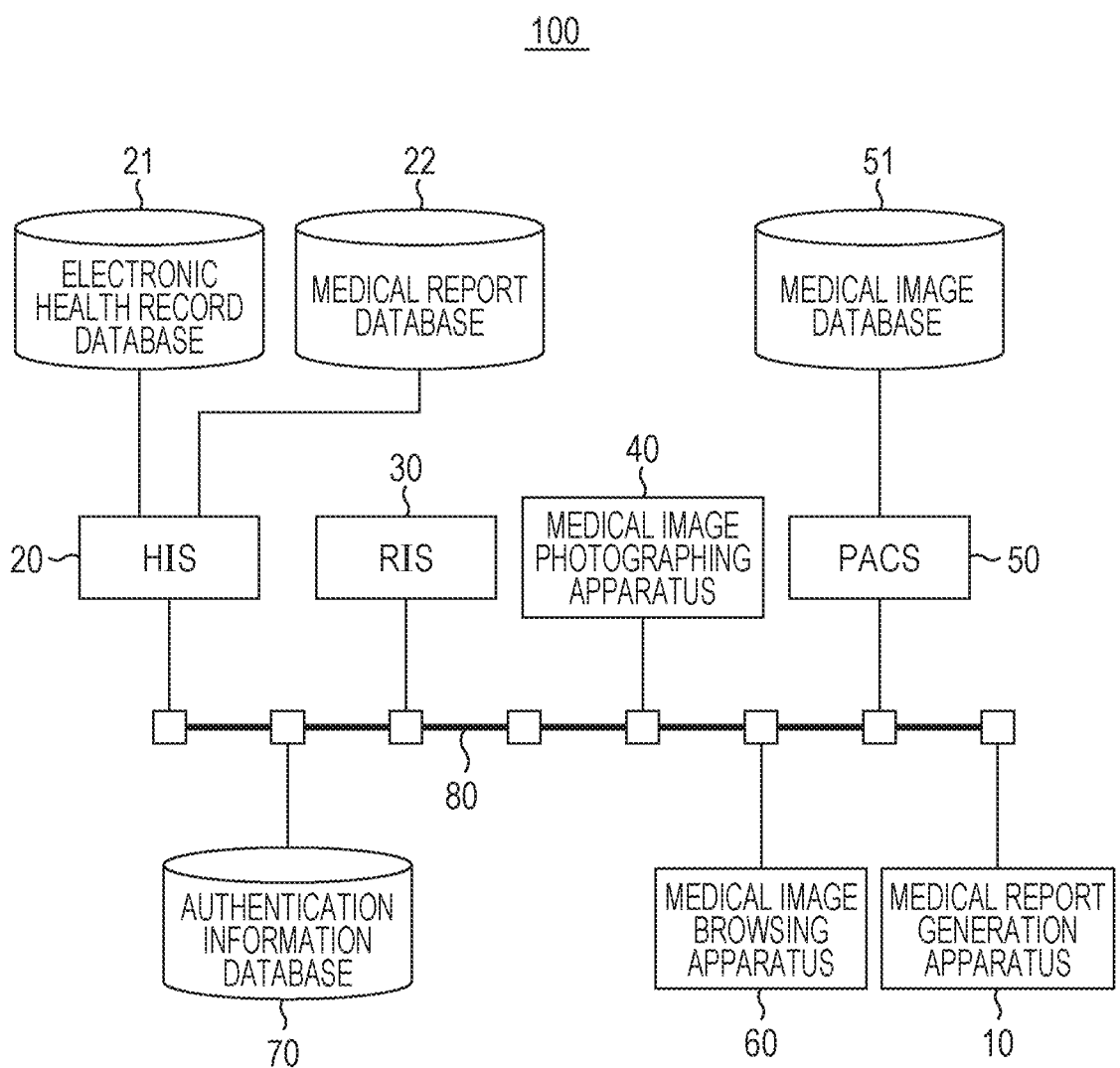
FIG. 1 is a diagram schematically illustrating a configuration of a medical report generation system according to a first embodiment.

FIG. 1 is a diagram schematically illustrating a configuration of a medical report generation system 100 according to the first embodiment.

The medical report generation system 100 includes, as illustrated in FIG. 1, a medical report generation apparatus 10, a hospital information system (HIS) 20, a radiology information system (RIS) 30, a medical image photographing apparatus 40, a picture archiving and communication system (PACS) 50, a medical image browsing apparatus 60, an authentication information database 70, and a network 80.

The medical report generation apparatus 10 generates a medical report.

The HIS 20 is a comprehensive system including a medical accounting system, a medical examination reservation system, and a medical examination information system, and includes an electronic health record database 21 and a medical report database 22. The electronic health record database 21 stores electronic health records which record medical examination information of patients. The medical report database 22 stores medical reports generated by the medical report generation apparatus 10 and the like.

The RIS 30 performs photographing reservation, image reading management, material stock control, and the like in a radiology department. The RIS 30 may manage the medical report database 22.

The medical image photographing apparatus 40 captures a medical image. The medical image photographing apparatus 40 is a generic term of a simple X-ray radiographing apparatus (or an X-ray imaging apparatus), a computed tomography (CT) apparatus, a magnetic resonance imaging (MRI) apparatus, a position emission tomography (PET) apparatus, a PET/CT apparatus, a single photon emission computed tomography (SPECT) apparatus, an ultrasonic image diagnosis apparatus, a fundus camera (or a fundus photographing apparatus), and an optical coherence tomography (OCT) apparatus, for example. An arbitrary number of such medical image photographing apparatuses 40 are installed for each medical institution.

The PACS 50 electronically performs storage, search, and communication of a medical image captured by the medical image photographing apparatus 40 and includes a medical image database 51 which stores medical images.

The medical image browsing apparatus 60 is used by a doctor to browse a medical image.

The authentication information database 70 stores authentication information for authentication of a user of the medical report generation system 100. For example, a user name, a password, and personal information of the user which are associated with each other are stored as the authentication information. Examples of the personal information of the user include a name, a department, and contact information.

The medical report generation apparatus 10, the HIS 20, the RIS 30, the medical image photographing apparatus 40, the PACS 50, the medical image browsing apparatus 60, and the authentication information database 70 are connected to the network 80 so as to communicate with one another.

Hardware Configuration of Medical Report Generation Apparatus

Figure 2:
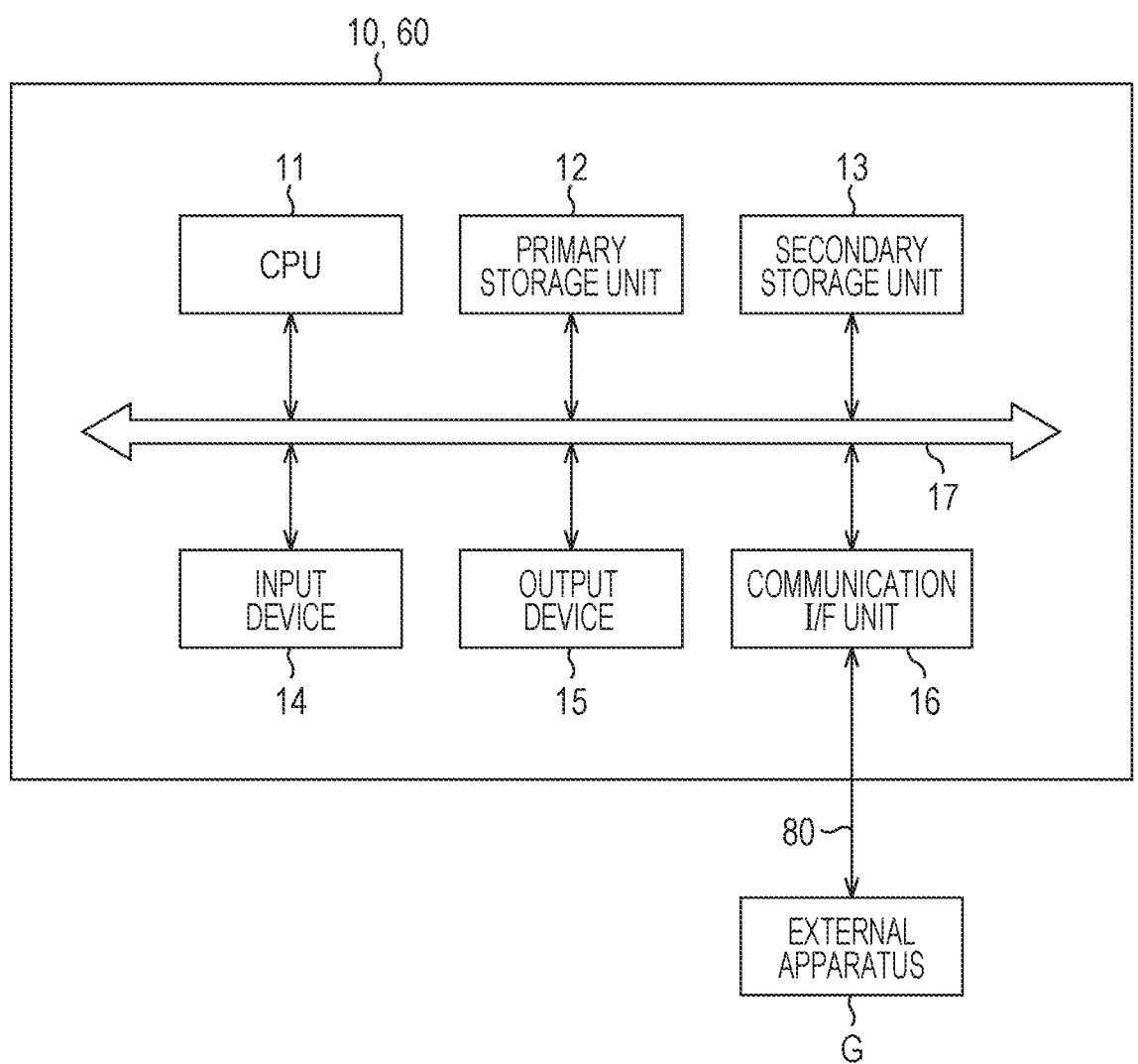
FIG. 2 is a diagram illustrating a hardware configuration of a medical report generation apparatus according to the first embodiment.

FIG. 2 is a diagram illustrating a hardware configuration of a medical report generation apparatus 10 according to the first embodiment.

The medical report generation apparatus 10 has a hardware configuration, as illustrated in FIG. 2, including a CPU 11, a primary storage unit 12, a secondary storage unit 13, an input device 14, an output device 15, a communication I/F unit 16, and a system bus 17.

The CPU 11 executes programs stored in the secondary storage unit 13 (including programs read by the primary storage unit 12 from the secondary storage unit 13) so as to control entire operation of the medical report generation apparatus 10 and perform various processes.

The primary storage unit 12 is a memory, such as a RAM, and reads and stores the programs, data, and the like stored in the secondary storage unit 13.

The secondary storage unit 13 is a storage medium, such as a hard disk or a flash memory. In general, memory capacity of the primary storage unit 12 is smaller than that of the secondary storage unit 13, and programs, data, and the like beyond the capacity of the primary storage unit 12 are stored in the secondary storage unit 13. Data to be stored for a long period of time is also stored in the secondary storage unit 13. In this embodiment, programs to execute processing procedures are stored in the secondary storage unit 13, and are read into the primary storage unit 12 when the programs are to be executed by the CPU 11.

The input device 14 includes a pointing device, such as a mouse, a touch panel, and a keyboard.

The output device 15 includes a monitor, such as an LCD, and a printer. A plurality of number of monitors may be used in combination as the output device 15.

The communication I/F unit 16 controls communication with an external apparatus G through the network 80.

The CPU 11, the primary storage unit 12, the secondary storage unit 13, the input device 14, the output device 15, and the communication I/F unit 16 are connected to the system bus 17 so as to communicate with one another.

Hardware Configuration of Medical Image Browsing Apparatus

In this embodiment, as with the medical report generation apparatus 10, the medical image browsing apparatus 60 of FIG. 1 also has the hardware configuration of FIG. 2.

Data Configuration of Medical Report

FIGS. 3A and 3B are diagrams illustrating data configurations of a medical report generated by the medical report generation apparatus 10 according to the first embodiment.

As illustrated in FIG. 3A, medical report data 300 generated by the medical report generation apparatus 10 includes patient information 310, examination information 320, client information 330, image reading basic information 340, and findings/diagnosis information 350.

The patient information 310 stores information on an examined patient. The patient information 310 includes, for example, a patient ID, a name, an age, and a medical history.

The examination information 320 stores information on a performed examination, such as an examined portion and a photographing protocol.

The client information 330 stores information on a department and a name of a clinician, contact information of the clinician, and information on a comment of the clinician.

The image reading basic information 340 stores information on a department and a name of an image reading doctor who generates the medical report and contact information of the image reading doctor.

The findings/diagnosis information 350 stores information on a region specified in a medical image (hereinafter referred to as a "target region") (target region information) and information on findings and diagnosis. The target region information and the information on findings and diagnosis are associated with each other. As the region information, a region ID of the target region stored in the medical image browsing apparatus 60 (specifically, a region information storage unit 620 illustrated in FIG. 5) is obtained and used where appropriate. Examples of the region information further include a representative image and image processing information. Furthermore, the information on findings is stored in a form in which text about one lesion corresponds to one item. Similarly, the information on diagnosis is stored in a form in which text about one disease corresponds to one item.

FIG. 3B is a diagram illustrating a table of the findings/diagnosis information 350 of FIG. 3A. Information on an item ID, a type, content, and an associated item ID is included in the table of the findings/diagnosis information 350 illustrated in FIG. 3B. Note that, although the findings/diagnosis information 350 is illustrated as the table in FIG. 3B, a data format is not limited to a table as long as the data has equivalent information. For example, the findings/diagnosis information 350 may be stored in a format of the medical report data 300 defined by an extensible markup language (XML).

Functional Configuration of Medical Report Generation Apparatus

Figure 4:
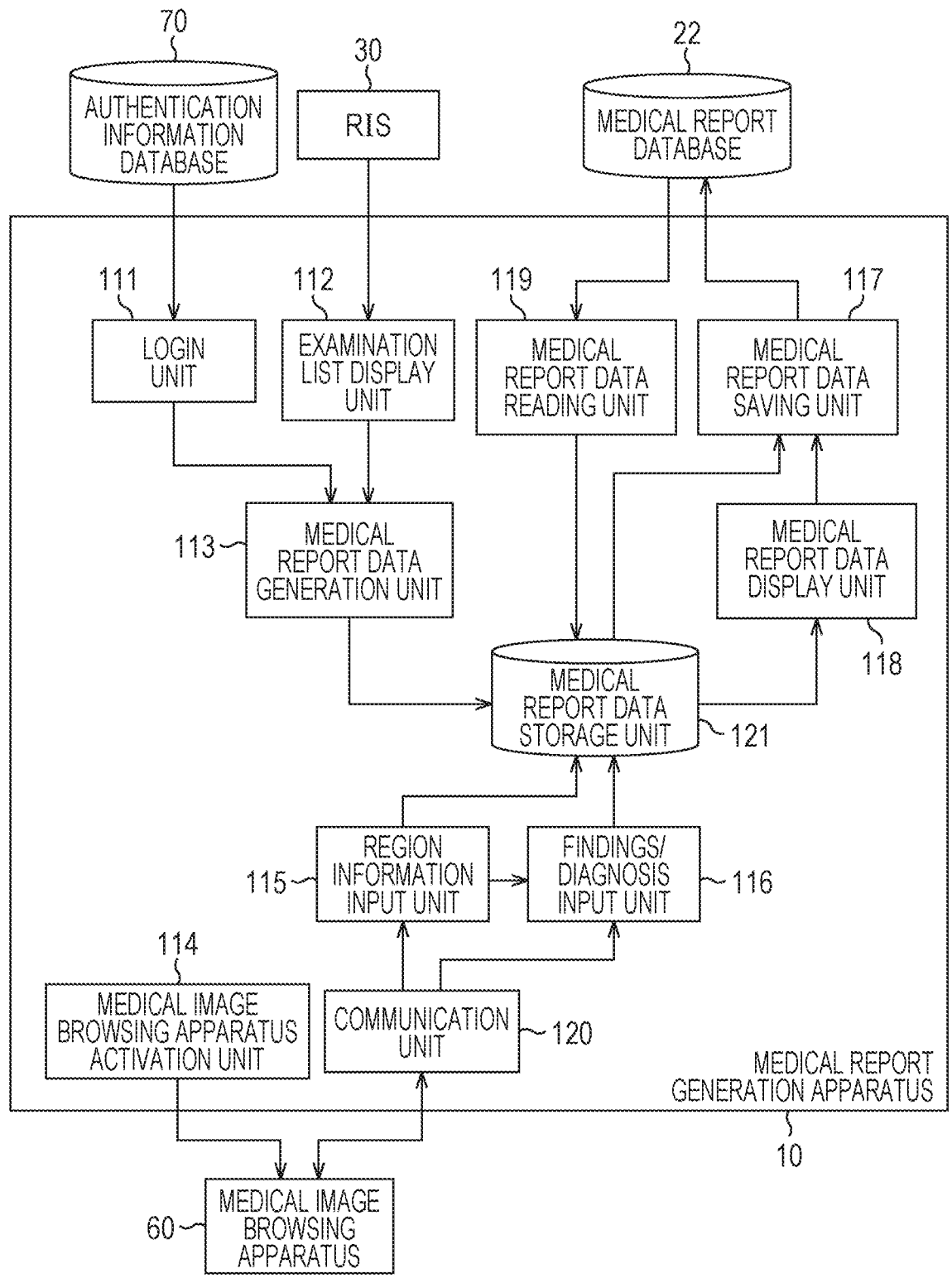
FIG. 4 is a diagram illustrating a functional configuration of the medical report generation apparatus according to the first embodiment.

FIG. 4 is a diagram illustrating a functional configuration of the medical report generation apparatus 10 according to the first embodiment. The medical report generation apparatus 10 generates the medical report data 300 including the information on the target region specified in the medical image as illustrated in FIG. 3A.

The medical report generation apparatus 10 includes, as illustrated in FIG. 4, a functional configuration including a login unit 111, an examination list display unit 112, a medical report data generation unit 113, a medical image browsing apparatus activation unit 114, a region information input unit 115, a findings/diagnosis input unit 116, a medical report data saving unit 117, a medical report data display unit 118, a medical report data reading unit 119, a communication unit 120, and a medical report data storage unit 121.

An example of the correspondence relationship between the hardware configuration of the medical report generation apparatus 10 illustrated in FIG. 2 and the functional configuration of the medical report generation apparatus 10 illustrated in FIG. 4 will be described hereinafter.

For example, the CPU 11, the programs stored in the secondary storage unit 13, the input device 14, and the communication I/F unit 16 illustrated in FIG. 2 configure the login unit 111, the medical image browsing apparatus activation unit 114, the medical report data saving unit 117, the medical report data reading unit 119, and the communication unit 120 illustrated in FIG. 4. Furthermore, the CPU 11, the programs stored in the secondary storage unit 13, the input device 14, the output device 15, and the communication I/F unit 16 illustrated in FIG. 2 configure the examination list display unit 112 illustrated in FIG. 4, for example. Moreover, the CPU 11 and the programs stored in the secondary storage unit 13 illustrated in FIG. 2 configure the medical report data generation unit 113, the region information input unit 115, and the findings/diagnosis input unit 116 illustrated in FIG. 4, for example. The CPU 11, the programs stored in the secondary storage unit 13, the input device 14, and the output device 15 illustrated in FIG. 2 configure the medical report data display unit 118 illustrated in FIG. 4, for example. The primary storage unit 12 and the secondary storage unit 13 illustrated in FIG. 2 configure the medical report data storage unit 121 illustrated in FIG. 4, for example.

The login unit 111 allows input of a user name and a password through the input device 14. When the input user name and the input password coincide with content stored in advance in the authentication information database 70, the medical report generation apparatus 10 becomes usable.

The examination list display unit 112 obtains a list of examinations for which medical reports are to be generated from the RIS 30 and displays the list in the output device 15 of the medical report generation apparatus 10. Here, the examination list display unit 112 changes a state of display of each examination in accordance with a result of a determination as to whether an image of the examination has been captured and a determination as to whether medical report data corresponding to the examination has been generated. Furthermore, the examination list display unit 112 changes a state of display of each examination in accordance with a status of generation of medical report data when the medical report data corresponding to the examination has been generated.

The medical report data generation unit 113 generates medical report data corresponding to an arbitrary examination and stores the medical report data in the medical report data storage unit 121. Here, the medical report data generated by the medical report data generation unit 113 has the data configuration illustrated in FIGS. 3A and 3B. Here, all content of the patient information 310, the examination information 320, and the client information 330 is obtained from the RIS 30. All content of the image reading basic information 340 is obtained from the authentication information database 70.

The medical image browsing apparatus activation unit 114 activates the medical image browsing apparatus 60. Simultaneously, the medical image browsing apparatus activation unit 114 notifies the medical image browsing apparatus 60 of the user name and the password input by the login unit 111 or the like information.

The region information input unit 115 obtains the information on the target region specified in the medical image through the communication unit 120 and supplies the region information to the findings/diagnosis input unit 116 and the medical report data storage unit 121. Specifically, the region information input unit 115 obtains the region information from the medical image browsing apparatus 60 (that is, the region information storage unit 620 of FIG. 5).

The findings/diagnosis input unit 116 inputs information on findings and diagnosis on the target region associated with the region information input by the region information input unit 115. Specifically, the findings/diagnosis input unit 116 associates the information on the findings and the diagnosis and the region information of an input target with each other and supplies the information to the medical report data storage unit 121 as finding/diagnosis information of the medical report data (the findings/diagnosis information 350 of FIG. 3A).

The medical report data saving unit 117 saves the medical report data stored in the medical report data storage unit 121 in the medical report database 22 through the HIS 20.

The medical report data display unit 118 displays the medical report data stored in the medical report data storage unit 121 in the output device 15 of the medical report generation apparatus 10.

The medical report data reading unit 119 reads arbitrary medical report data from the medical report database 22 through the HIS 20 and stores the medical report data in the medical report data storage unit 121.

The communication unit 120 communicates with the medical image browsing apparatus 60 through the network 80.

The medical report data storage unit 121 stores the medical report data.

Functional Configuration of Medical Image Browsing Apparatus

Figure 5:
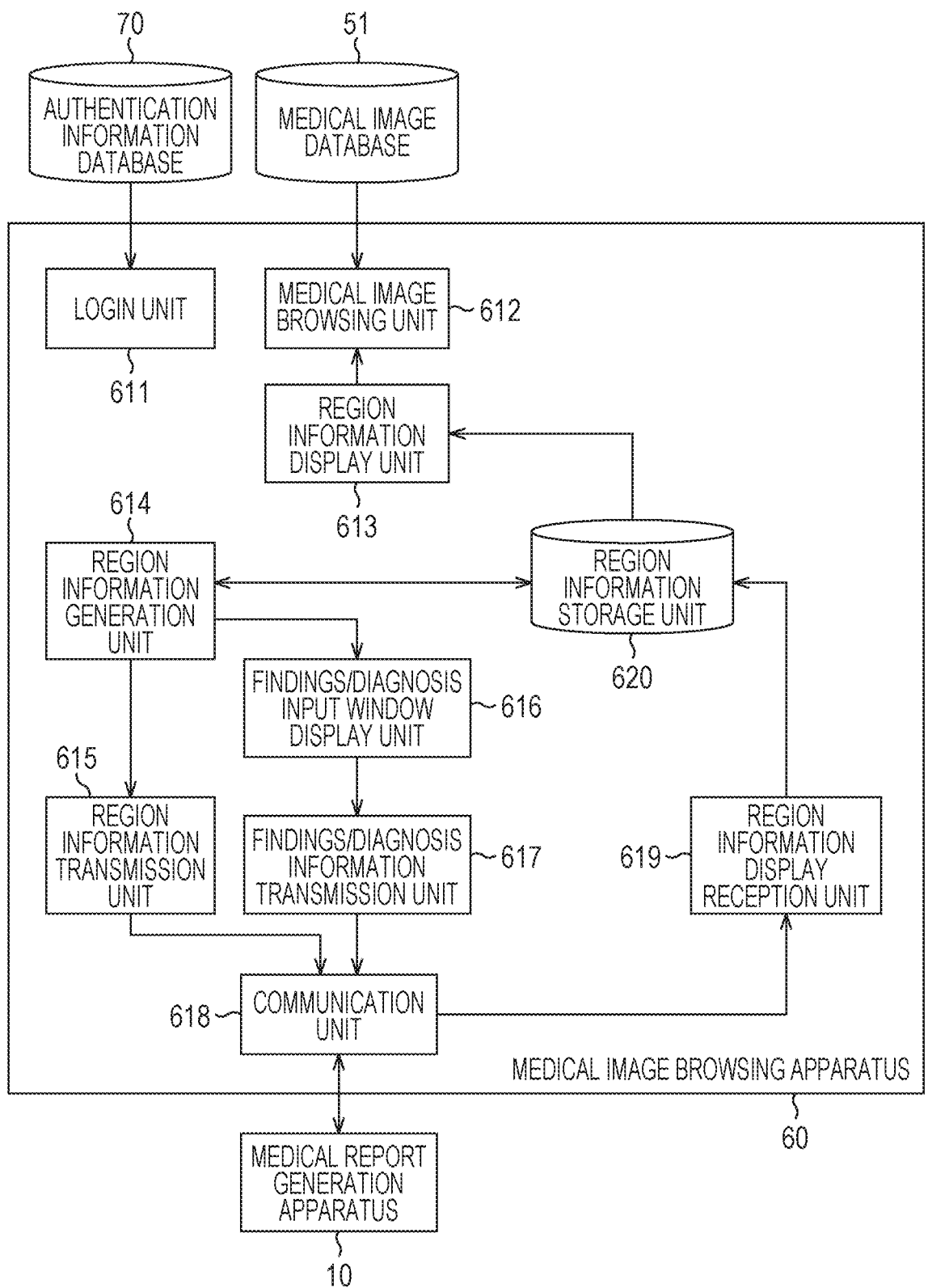
FIG. 5 is a diagram illustrating a functional configuration of a medical image browsing apparatus according to the first embodiment.

FIG. 5 is a diagram illustrating a functional configuration of the medical image browsing apparatus 60 according to the first embodiment.

The medical image browsing apparatus 60 has, as illustrated in FIG. 5, a functional configuration including a login unit 611, a medical image browsing unit 612, a region information display unit 613, a region information generation unit 614, a region information transmission unit 615, a findings/diagnosis input window display unit 616, a findings/diagnosis information transmission unit 617, a communication unit 618, a region information display reception unit 619, and the region information storage unit 620.

An example of the correspondence relationship between the hardware configuration of the medical image browsing apparatus 60 illustrated in FIG. 2 and the functional configuration of the medical image browsing apparatus 60 illustrated in FIG. 5 is described hereinafter.

The CPU 11, the programs stored in the secondary storage unit 13, the input device 14, and the communication I/F unit 16 illustrated in FIG. 2 configure the login unit 611 and the communication unit 618 illustrated in FIG. 5, for example. Furthermore, the CPU 11, the programs stored in the secondary storage unit 13, the input device 14, the output device 15, and the communication I/F unit 16 illustrated in FIG. 2 configure the medical image browsing unit 612 illustrated in FIG. 5, for example. The CPU 11, the programs stored in the secondary storage unit 13, the input device 14, and the output device 15 illustrated in FIG. 2 configure the region information display unit 613 and the findings/diagnosis input window display unit 616 illustrated in FIG. 5, for example. The CPU 11, the programs stored in the secondary storage unit 13, and the input device 14 illustrated in FIG. 2 configure the region information generation unit 614, the region information transmission unit 615, the findings/diagnosis information transmission unit 617, and the region information display reception unit 619 illustrated in FIG. 5, for example. The primary storage unit 12 and the secondary storage unit 13 illustrated in FIG. 2 configure the region information storage unit 620 illustrated in FIG. 5, for example.

The login unit 611 allows input of a user name and a password through the input device 14. When the input user name and the input password coincide with content stored in advance in the authentication information database 70, the medical image browsing apparatus 60 becomes usable.

The medical image browsing unit 612 reads a medical image to be browsed or an image series associated with a plurality of images included in the medical image (or a plurality of sliced images when the medical image is a CT image, for example) from the medical image database 51 through the PACS 50 and displays the medical image or the image series in the output device 15 for browsing. The medical image browsing unit 612 executes various processes associated with image browsing including a change of an image to be displayed and application of image processing in accordance with an operation performed by a doctor through the input device 14.

The region information display unit 613 displays the region information stored in the region information storage unit 620 such that the region information overlaps with the medical image. The region information display unit 613 may display, when a sliced image before or after a sliced image including the target region associated with the region information in the same image series is displayed, information indicating that the target region is located near the sliced image.

The region information generation unit 614 generates region information (target region information) to be displayed in the medical image in response to the specifying of the target region performed by the doctor through the input device 14. The region information generation unit 614 assigns a region ID to the generated region information and associates the region ID with an address of an image in which the region information is generated, positional information of the target region, applied image processing information, region rendering information including colors and thicknesses of lines to be used when the region information is rendered, a representative image including one or more indicators each of which representing the target region, and a group ID and stores the associated region ID in the region information storage unit 620.

Here, the positional information is represented by a relative coordinate of an image. Note that the "region information (the target region information)" collectively indicates information on the region ID, the image address, the positional information, the image processing information, the region rendering information, the representative image, and the group ID hereinafter. Region information in the same group has the same group ID.

The region information storage unit 620 stores the region information.

FIG. 6 is a diagram illustrating the region information stored in the region information storage unit 620 of FIG. 5. As illustrated in FIG. 6, the region information includes a region ID, an image address, positional information, image processing information, region rendering information, a representative image, and a group ID. It is assumed here that a medical image including an indicator (not illustrated in FIG. 6) indicating the target region specified in the medical image is referred to as the "representative image" in this embodiment. Furthermore, the group ID is group information indicating a group of the region information associated with the target region specified in the medical image in this embodiment.

Note that, although coordinates of a region of the region information are denoted in a two-dimensional manner in FIG. 6, the coordinates may be denoted in a three-dimensional manner. In a case where images which are continuous to the image including the region corresponding to the region information in time series exist, the region information may be automatically generated in the same position in the images. In this case, the generated region information may be managed as individual region information or the same region information. Furthermore, a plurality of images obtained in different time points may be stored as representative images.

In this embodiment, an image captured when the region information is generated is stored as the representative image. Specifically, in a case where a plurality of target regions are included in the same medial image, region information of the individual target regions are included in a representative image. Here, a display state of the region information corresponding to a certain region ID differs from a display state of the other region information. By this, it may be recognized that a target region represented by a certain representative image is one of the target regions only by viewing the representative image.

Figure 7:
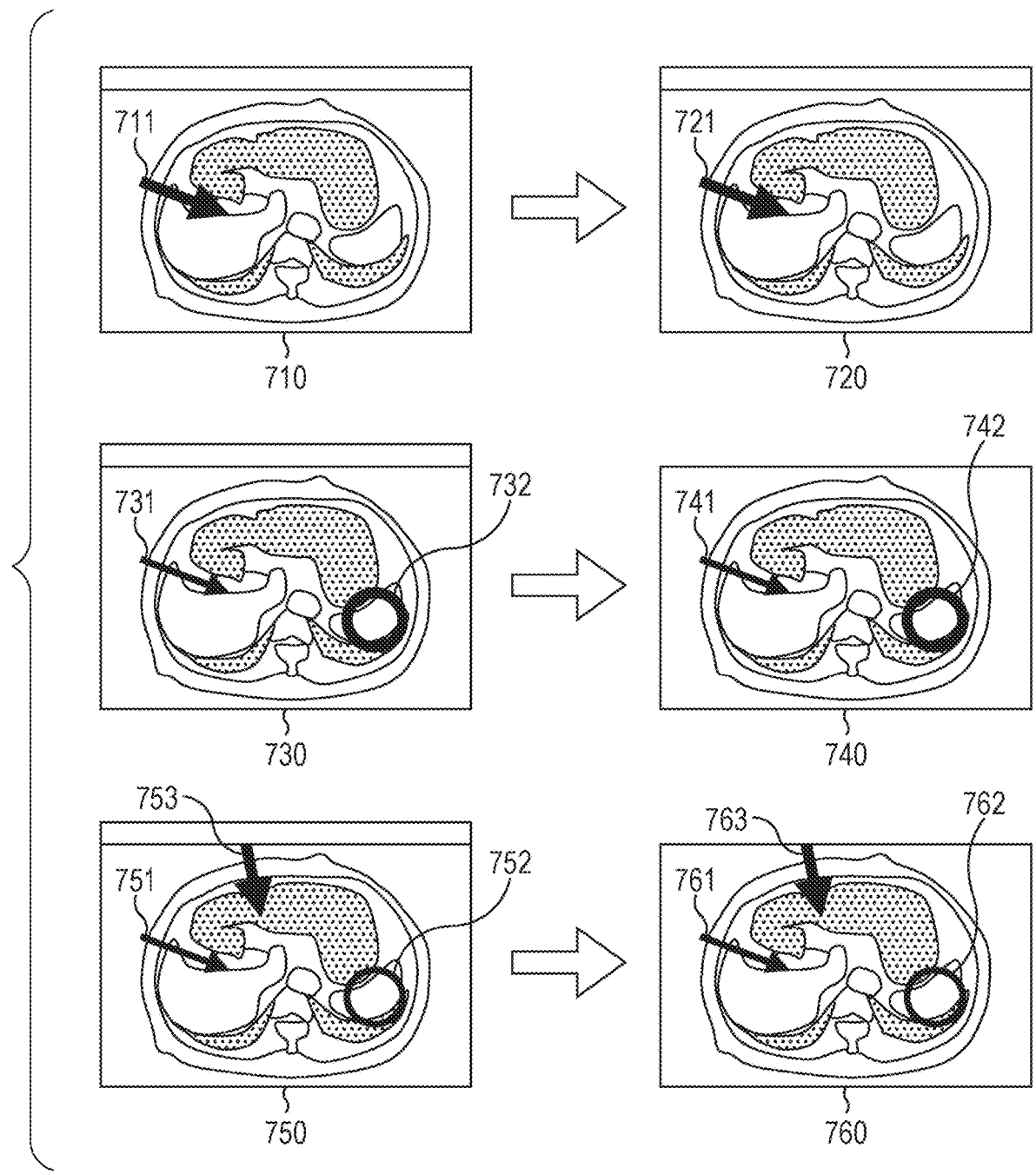
FIG. 7 is a diagram illustrating representative images included in the region information according to the first embodiment.

FIG. 7 is a diagram illustrating representative images included in the region information according to the first embodiment.

On a left side in FIG. 7, medical images 710, 730, and 750 displayed in the output device 15 of the medical image browsing apparatus 60 are illustrated. Furthermore, in FIG. 7, medical images 710, 730, and 750 are displayed in the output device 15 in this order as time proceeds. The medical image 710 includes an indicator 711 indicating a target region specified by the doctor through the input device 14. The medical image 730 includes, in addition to an indicator 731 based on the indicator 711 in the medical image 710, an indicator 732 indicating a target region specified next by the doctor through the input device 14. In this case, a display state of the indicator 732 is different from that of the indicator 731. Furthermore, in the example of FIG. 7, the indicator 732 is thickly indicated so as to clarify the region specified at this time point and the indicator 731 is thinly indicated (thinner than the indicator 711). The medical image 750 includes, in addition to an indicator 751 based on the indicator 731 in the medical image 730 and an indicator 752 based on the indicator 732 in the medical image 730, an indicator 753 indicating a target region specified next by the doctor through the input device 14. In this case, a display state of the indicator 753 is different from those of the indicators 751 and 752. Furthermore, in the example of FIG. 7, the indicator 753 is thickly indicated so as to clarify the region specified at this time point and the indicators 751 and 752 are thinly indicated. It is assumed here that the medical images 710, 730, and 750 have the same content and only the indicators included in the medical images 710, 730, and 750 are different from one another in this embodiment. Furthermore, in this embodiment, the target regions in the individual medical images 710, 730, and 750 are specified by the doctor as a plurality of associated lesion regions.

On a right side in FIG. 7, representative images 720, 740, and 760 generated by the region information generation unit 614 are illustrated. The representative image 720 is captured when the region information of the representative image 720 is generated (when the medical image browsing apparatus 60 displays the medical image 710 in the example of FIG. 7). An indicator 721 based on the indicator 711 in the medical image 710 is included in the representative image 720. The representative image 740 is captured when the region information of the representative image 740 is generated (when the medical image browsing apparatus 60 displays the medical image 730 in the example of FIG. 7). An indicator 741 based on the indicator 731 included in the medical image 730 and an indicator 742 based on the indicator 732 included in the medical image 730 are included in the representative image 740. The representative image 760 is captured when the region information of the representative image 760 is generated (when the medical image browsing apparatus 60 displays the medical image 750 in the example of FIG. 7). An indicator 761 based on the indicator 751 included in the medical image 750, an indicator 762 based on the indicator 752 included in the medical image 750, and an indicator 763 based on the indicator 753 included in the medical image 750 are included in the representative image 760.

The individual region information stored in the region information storage unit 620 is automatically stored in the images including the corresponding indicators indicating the target regions as metadata. When the image has a DICOM format, the region information may be stored as a DICOM tag. Furthermore, when a medical image is displayed by the medical image browsing unit 612, the region information generation unit 614 obtains region information associated with a target region indicated by an indicator in the medical image and automatically stores the region information in the region information storage unit 620.

The region information transmission unit 615 transmits the region information stored in the region information storage unit 620 to the medical report generation apparatus 10 through the communication unit 618.

The findings/diagnosis input window display unit 616 displays a window for inputting and editing information on findings and diagnosis for the region information generated by the region information generation unit 614.

The findings/diagnosis information transmission unit 617 transmits content input to the window displayed by the findings/diagnosis input window display unit 616 to the medical report generation apparatus 10 through the communication unit 618.

The communication unit 618 communicates with the medical report generation apparatus 10 through the network 80.

The region information display reception unit 619 receives region information or a region ID from an external apparatus on the network 80 through the communication unit 618. When the same region information is included in the region information storage unit 620, the region information display reception unit 619 causes the medical image browsing unit 612 to display an image corresponding to the region information. Here, the region information display reception unit 619 successively performs reading of an image corresponding to an address stored in the region information, a process of rendering a region using positional information and rendering information, and a process of applying image processing information. Note that the region information received by the region information display reception unit 619 is displayed so as to be distinguishable from other region information. When region information the same as the region information externally transmitted is not included in the region information storage unit 620, the region information display reception unit 619 adds the region information to the region information storage unit 620 and performs the display process described above.

Figure 8:
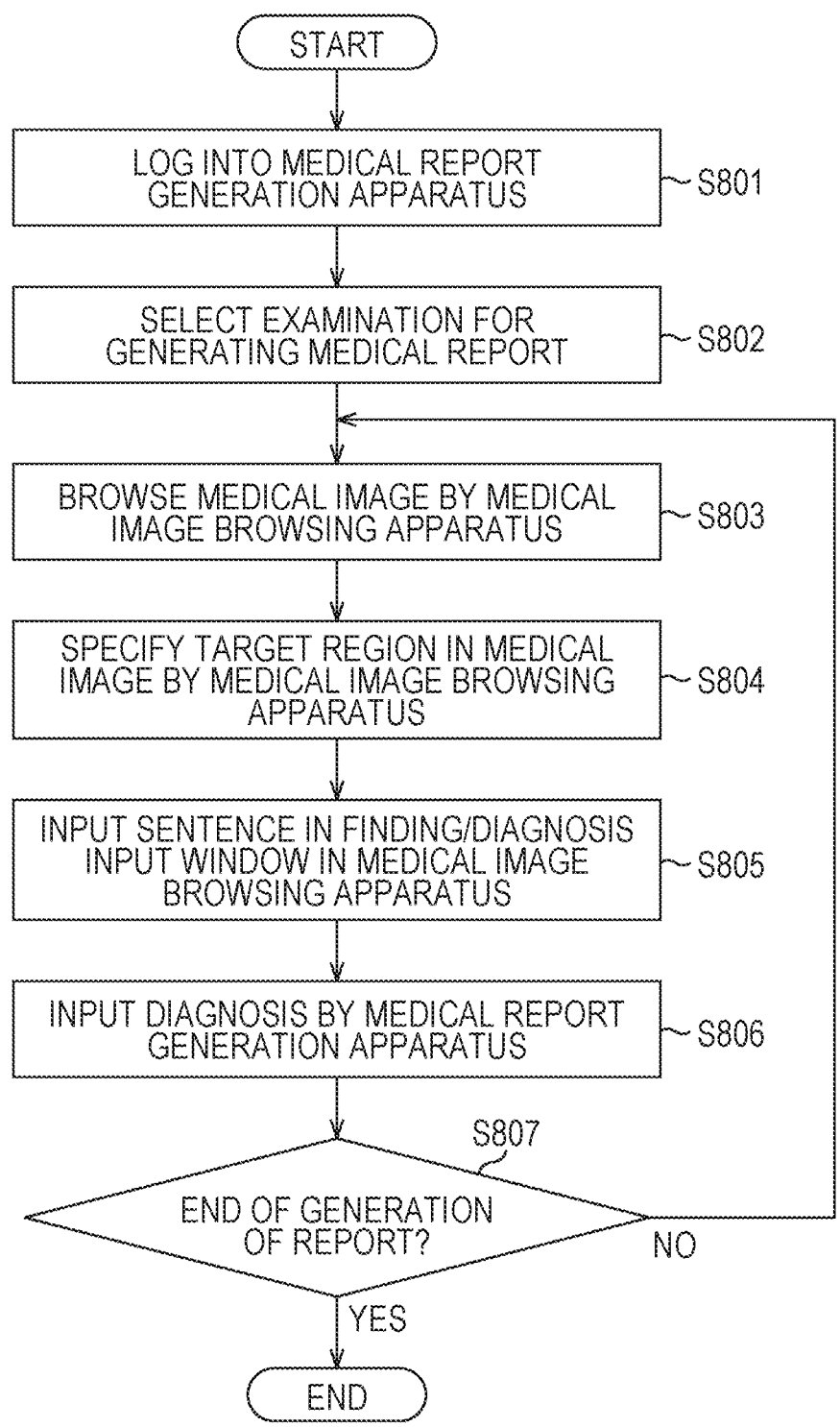
FIG. 8 is a flowchart of a procedure of a medical report generation process performed by the medical report generation system according to the first embodiment.

Procedure of Medical Report Generation Process by Medical Report Generation System FIG. 8 is a flowchart of a procedure of a medical report generation process performed by the medical report generation system 100 according to the first embodiment.

In step S801, when an image reading doctor performs login by inputting a user name and a password using the input device 14 of the medical report generation apparatus 10, the login unit 111 of the medical report generation apparatus 10 performs a login process. Specifically, when the input user name and the input password coincide with content stored in advance in the authentication information database 70, the login unit 111 causes the medical report generation apparatus 10 to become usable.

FIGS. 9A, 9B, 10A, and 10B are diagrams illustrating GUI screens used in the medical report generation process performed by the medical report generation system 100 according to the first embodiment.

Figure 9A:
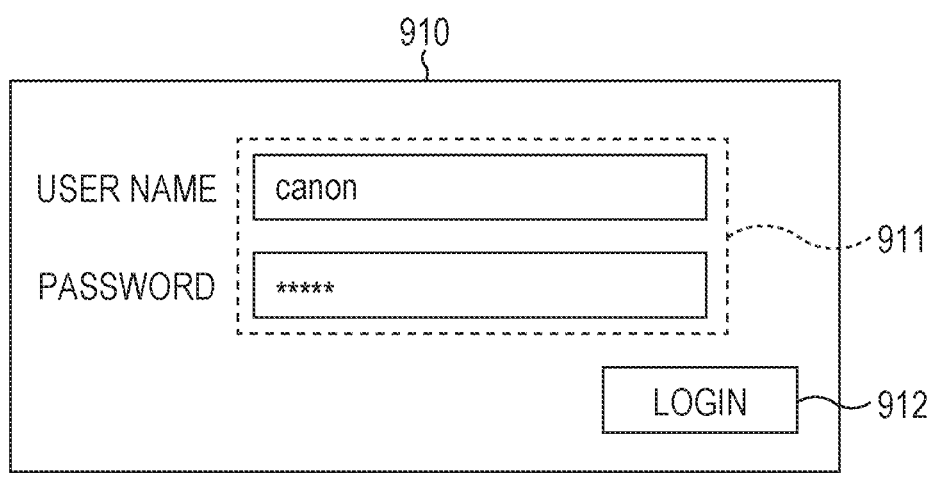

The login in step S801 is performed when the image reading doctor inputs the user name and the password in a user information input section 911 and presses a login button 912 in a GUI screen 910 of FIG. 9A.

Thereafter, the examination list display unit 112 of the medical report generation apparatus 10 displays a GUI screen 920 of an examination list illustrated in FIG. 9B in the output device 15. The GUI screen 920 of the examination list illustrated in FIG. 9B includes a search condition input section 921, an examination list 922, and an execution button 923.

In step S802, when the image reading doctor selects an examination to generate a medical report, the medical report data generation unit 113 of the medical report generation apparatus 10 performs a process of specifying the selected examination. Here, the selection of an examination is performed when the image reading doctor selects one examination in the examination list 922 and presses the execution button 923 in the GUI screen 920 of FIG. 9B. Thereafter, the medical report data generation unit 113 of the medical report generation apparatus 10 generates medical report data corresponding to the specified examination.

Furthermore, the medical image browsing apparatus activation unit 114 of the medical report generation apparatus 10 activates the medical image browsing apparatus 60 at this time. Thereafter, the login unit 611 of the medical image browsing apparatus 60 performs a login process using the user name and the password input in step S801. When the medical image browsing apparatus 60 becomes usable as a result of the login process, the medical image browsing unit 612 of the medical image browsing apparatus 60 reads a medical image captured in the examination selected in step S802 from the medical image database 51 as a browsing target medical image. Although the medical image browsing unit 612 of the medical image browsing apparatus 60 automatically determines the browsing target medical image in this embodiment, other methods may be employed. For example, in a case where the selected examination has a series of a plurality of images, the series of a plurality of images may be displayed as a list and the user may select one of the plurality of images in the series to browse. Alternatively, the series of a plurality of images may be simultaneously arranged for browsing.

Subsequently, in step S803, the medical image browsing unit 612 of the medical image browsing apparatus 60 displays the browsing target medical image read in step S802 in the output device 15 of the medical image browsing apparatus 60 in a browsing available manner. By this, the image reading doctor may browse the browsing target medical image.

Figure 10A:
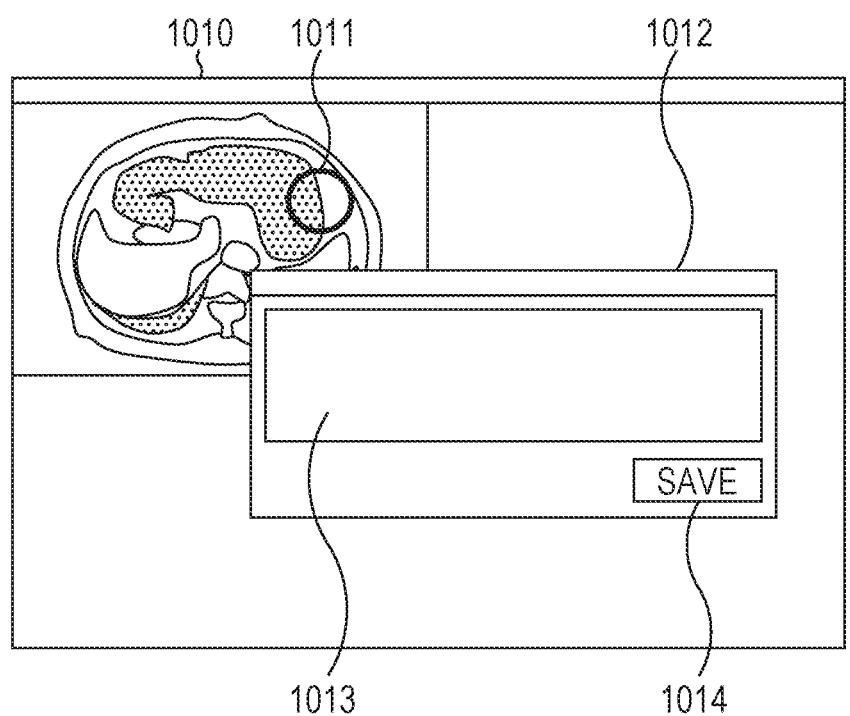

Subsequently, when the image reading doctor specifies a target region in the browsing target medical image in step S804, the region information generation unit 614 of the medical image browsing apparatus 60 detects the specifying of a target region. Here, the specifying of a target region by the image reading doctor is performed by an operation of drag-and-drop of a mouse on the browsing target medical image, for example. Thereafter, the region information generation unit 614 of the medical image browsing apparatus 60 groups the region information in a method to be described with reference to FIG. 11. The region information generation unit 614 of the medical image browsing apparatus 60 performs a process of updating a representative image of the region information in the same group in a method to be described with reference to FIG. 12, for example. The findings/diagnosis input window display unit 616 of the medical image browsing apparatus 60 displays a window to input findings of the generated region information such that the window overlaps with the image. In FIG. 10A, an example of a GUI screen 1010 displayed in the medical image browsing apparatus 60 is illustrated.

Subsequently, in step S805, when the image reading doctor inputs findings, the findings/diagnosis information transmission unit 617 of the medical image browsing apparatus 60 detects the input. The image reading doctor performs the input of findings by inputting text in a text input section 1013 of a findings/diagnosis input window 1012 of FIG. 10A and pressing a saving button 1014.

Thereafter, the region information transmission unit 615 of the medical image browsing apparatus 60 transmits region information (target region information) corresponding to the target region specified in step S804 to the region information input unit 115 of the medical report generation apparatus 10 through the communication unit 618. Furthermore, the findings/diagnosis information transmission unit 617 of the medical image browsing apparatus 60 inputs the findings input in step S805 in the findings/diagnosis input unit 116 of the medical report generation apparatus 10 through the communication unit 618 as findings for the target region specified in step S804.

Figure 10B:
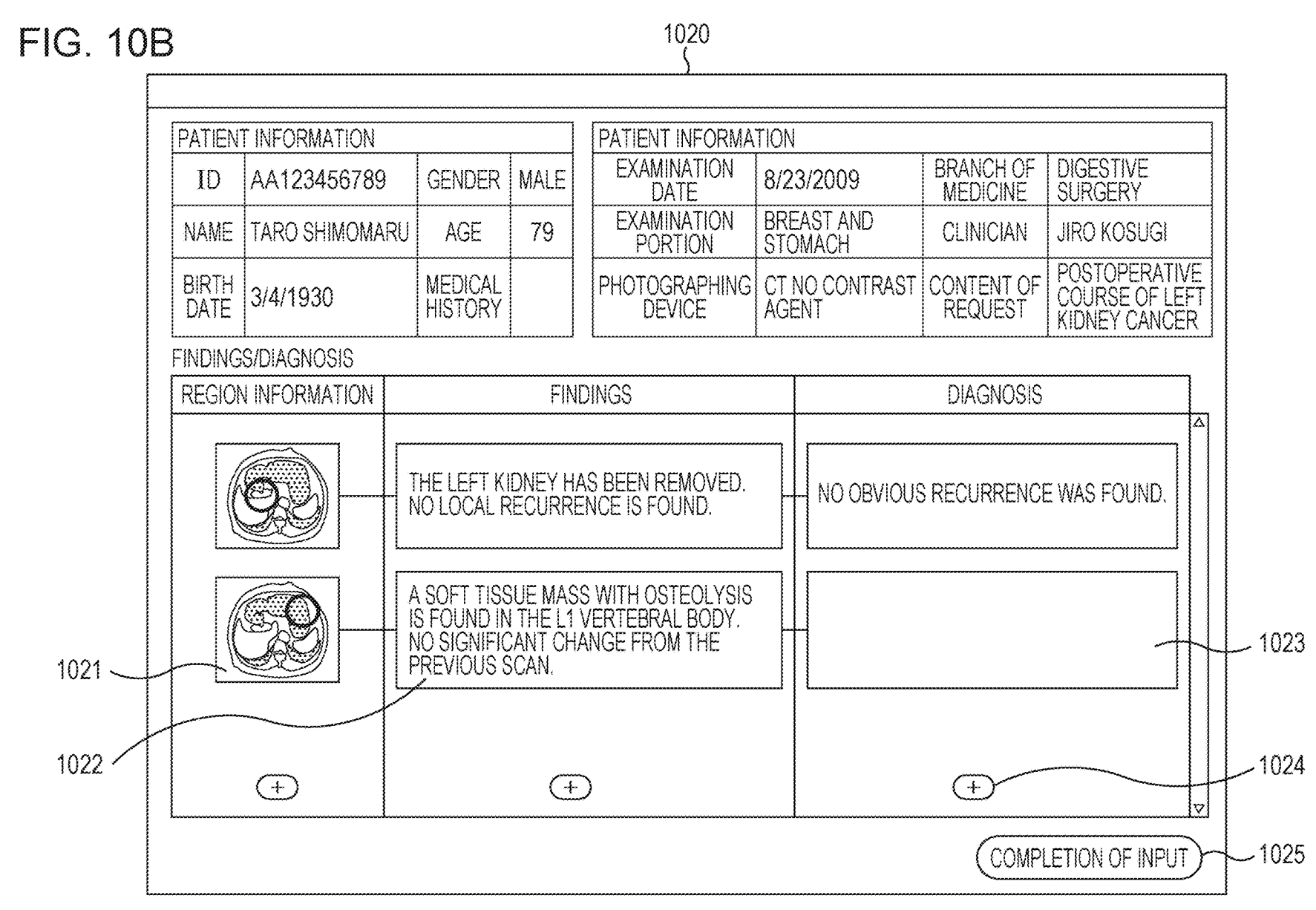

Thereafter, the medical report generation apparatus 10 manages the region information and the findings/diagnosis information which are simultaneously input and which are associated with each other. If the same region information has already been stored in the medical report generation apparatus 10, the region information is updated. The findings are similarly updated. In FIG. 10B, a GUI screen 1020 displayed in the medical report generation apparatus 10 at this time is illustrated. In the GUI screen 1020 of FIG. 10B, representative images of the region information input by the region information input unit 115 are displayed in a region information input section 1021. Furthermore, in the GUI screen 1020 of FIG. 10B, content input to the findings/diagnosis input unit 116 is displayed in a findings input section 1022 and a diagnosis input section 1023. Information is added downward in order of input. Alternatively, the information may be grouped in a unit of portion or in a unit of region.

Subsequently, in step S806, the findings/diagnosis input unit 116 of the medical report generation apparatus 10 inputs the diagnosis input by the image reading doctor using the input device 14 in the medical report data storage unit 121. The image reading doctor inputs the diagnosis by inputting text in the diagnosis input section 1023 of FIG. 10B. Note that, in the GUI screen 1020 of FIG. 10B, an input frame may be added using an input frame addition button 1024 and the content of the findings input section 1022 may be modified.

Subsequently, in step S807, the medical report data generation unit 113 of the medical report generation apparatus 10 determines whether the generation of the medical report data is to be terminated. Here, the medical report data generation unit 113 determines whether the generation of the medical report data is to be terminated in accordance with a result of a determination as to whether a findings/diagnosis input completion button 1025 of FIG. 10B has been pressed by the image reading doctor. When the determination is negative in step S807 (S807: No), the process returns to step S803 and the process in step S803 onwards is performed again. On the other hand, when the determination is affirmative in step S807 (S807: Yes), the medical report data saving unit 117 performs a process of saving the medical report data, and thereafter, the process in the flowchart of FIG. 8 is terminated.

Procedure of Region Information Grouping Process

Figure 11:
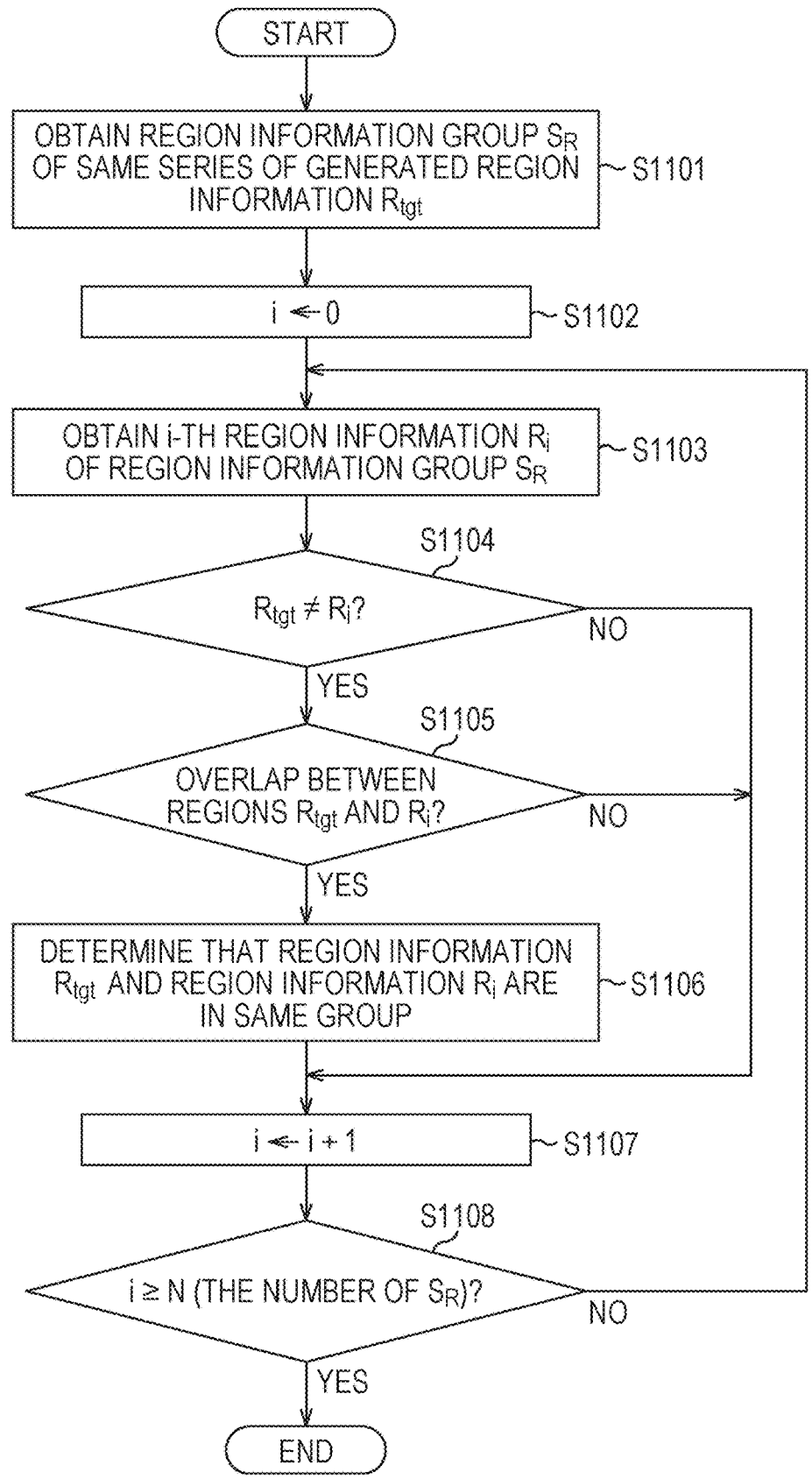
FIG. 11 is a flowchart of a procedure of a region information grouping process according to the first embodiment.

FIG. 11 is a flowchart illustrating a procedure of a region information grouping process according to the first embodiment. The flowchart of FIG. 11 illustrates a procedure of a process of grouping associated region information when the region information generation unit 614 of the medical image browsing apparatus 60 generates region information. In a description below, region information generated by the region information generation unit 614 is denoted by "$R_{tgt}$".

In step S1101, the region information generation unit 614 of the medical image browsing apparatus 60 obtains a region information group $S_R$ which is the same series as the region information $R_{tgt}$ among region information stored in the region information storage unit 620. It is assumed here that the number of region information included in the region information group $S_R$ is N.

In step S1102, the region information generation unit 614 of the medical image browsing apparatus 60 assigns 0 to a variable i indicating region information to be processed included in the region information group $S_R$.

In step S1103, the region information generation unit 614 of the medical image browsing apparatus 60 obtains i-th region information $R_i$ in the region information group $S_R$.

In step S1104, the region information generation unit 614 of the medical image browsing apparatus 60 determines whether the region information $R_{tgt}$ is different from the region information $R_i$. The difference determination of the region information is made by comparing region IDs with each other.

When the determination is affirmative in step S1104 (S1104: Yes), the process proceeds to step S1105.

In step S1105, the region information generation unit 614 of the medical image browsing apparatus 60 determines whether a region corresponding to the region information $R_{tgt}$ overlaps with a region corresponding to the region information $R_i$. Specifically, it is determined whether the region corresponding to the region information $R_{tgt}$ overlaps with a sliced image which includes the region corresponding to the region information $R_i$. If the regions are represented in a three dimensional manner, the determination is made in the three dimensional manner.

When the determination is affirmative as a result of the determination made in step S1105 (S1105: Yes), the process proceeds to step S1106.

In step S1106, the region information generation unit 614 of the medical image browsing apparatus 60 determines that the region information $R_{tgt}$ and the region information $R_i$ are in the same group. Specifically, in this embodiment, region information corresponding to target regions included in the same plane in a medical image is included in the same group, and the same value is input to group IDs of the region information.

When the process in step S1106 is terminated, when the determination is negative in step S1104 (S1104: No), or when the determination is negative in step S1105 (S1105: No), the process proceeds to step S1107.

In step S1107, the region information generation unit 614 of the medical image browsing apparatus 60 adds 1 to the variable i.

In step S1108, the region information generation unit 614 of the medical image browsing apparatus 60 determines whether the variable i is equal to or larger than N which corresponds to the number of region information included in the region information group $S_R$. When the determination is negative (S1108: No), the process returns to step S1103 and the process in step S1103 onwards is performed again.

On the other hand, when the determination is affirmative (S1108: Yes), the process of the flowchart in FIG. 11 is terminated.

By the process of the flowchart in FIG. 11 described above, all the region information included in the sliced image which is the same as the region information generated by the region information generation unit 614 is determined as the same group.

Figure 12:
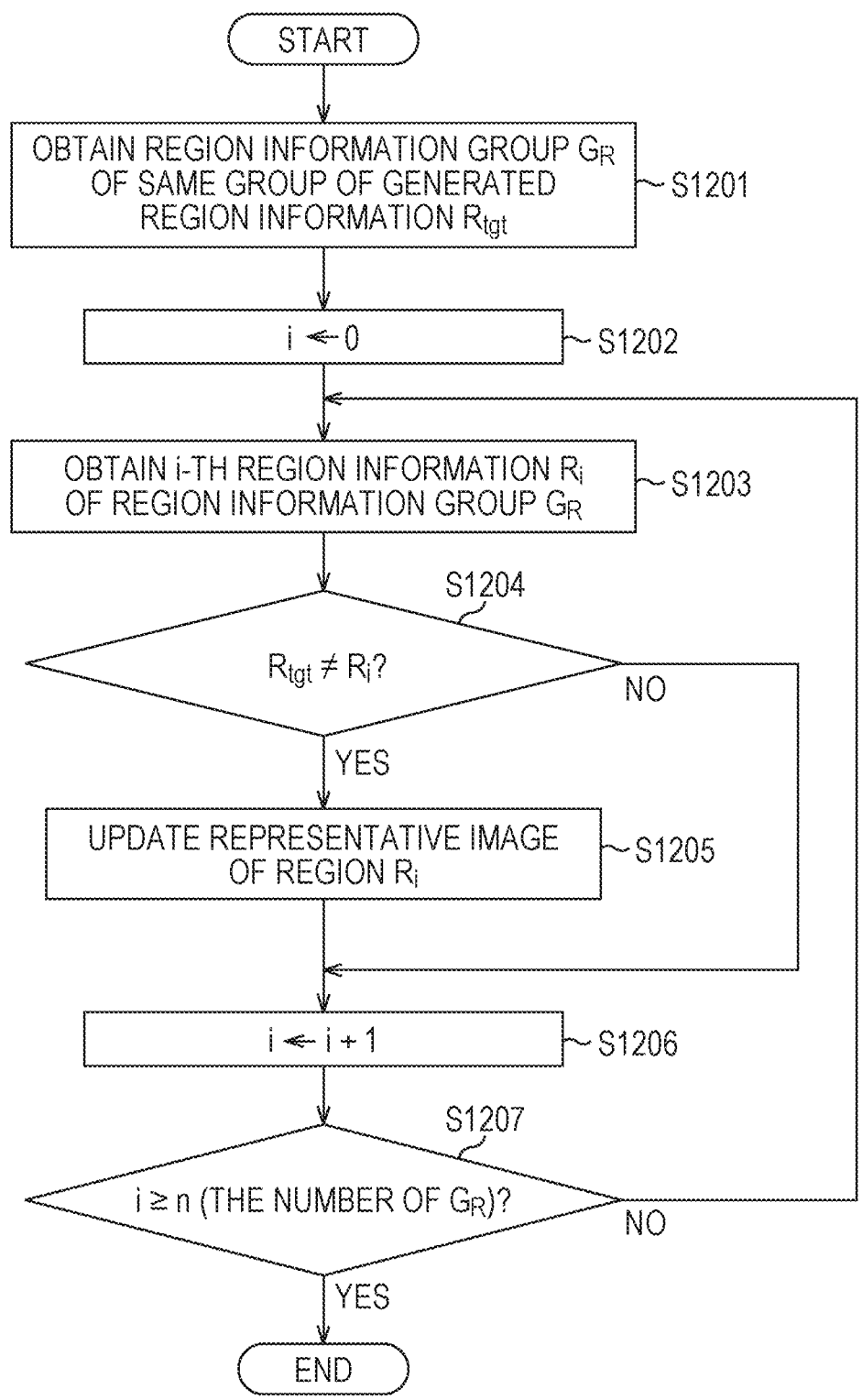
FIG. 12 is a flowchart of a procedure of a process of updating representative images of the region information which belongs to the same group according to the first embodiment.

Procedure of Process of Updating Representative Images of Region Information in Same Group FIG. 12 is a flowchart of a procedure of a process of updating a representative image of region information which belongs to the same group according to the first embodiment. The flowchart of FIG. 12 illustrates a procedure of a process of updating a representative image of region information included in the same group when the region information generation unit 614 of the medical image browsing apparatus 60 generates region information.

In step S1201, the region information generation unit 614 of the medical image browsing apparatus 60 obtains a region information group $G_R$ which includes the generated region information $R_{tgt}$ from the region information storage unit 620. It is assumed here that the number of region information(s) included in the region information group $G_R$ is n.

In step S1202, the region information generation unit 614 of the medical image browsing apparatus 60 assigns 0 to a variable i indicating region information to be processed included in the region information group $G_R$.

In step S1203, the region information generation unit 614 of the medical image browsing apparatus 60 obtains i-th region information $R_i$ in the region information group $G_R$.

In step S1204, the region information generation unit 614 of the medical image browsing apparatus 60 determines whether the region information $R_{tgt}$ is different from the region information $R_i$. The difference determination of the region information is made by comparing region IDs with each other.

When the determination is affirmative in step S1204 (S1204: Yes), the process proceeds to step S1205.

In step S1205, the region information generation unit 614 of the medical image browsing apparatus 60 applies image processing information of the region information $R_i$ to a sliced image including the region information $R_i$, captures an image in which a region corresponding to the region information $R_i$ is in a selection state (a display state), and updates and stores the image as a representative image of the region information $R_i$. It is assumed here that the sliced image which is a source of the capturing includes an indicator indicating a target region corresponding to the region information $R_i$ and indicators indicating target regions corresponding to other region information including the region information $R_{tgt}$ in a distinguishable manner. Furthermore, all of the steps of the process are performed in background and are not displayed in a screen of the medical image browsing apparatus 60.

When the process in step S1205 is terminated or when it is determined that the region information $R_{tgt}$ and the region information $R_i$ are the same as each other in step S1204 (S1204: No), the process proceeds to step S1206.

In step S1206, the region information generation unit 614 of the medical image browsing apparatus 60 adds 1 to the variable i.

In step S1207, the region information generation unit 614 of the medical image browsing apparatus 60 determines whether the variable i is equal to or larger than n which is the number of region information included in the region information group $G_R$. When the determination is negative (S1207: No), the process returns to step S1203 and the process in step S1203 onwards is performed again.

On the other hand, when the determination is affirmative (S1207: Yes), the process of the flowchart of FIG. 12 is terminated.

By the process in the flowchart of FIG. 12 described above, representative images may be updated such that all indicators indicating the target regions corresponding to the region information included in the same group are displayed in the representative images.

Thereafter, the region information generation unit 614 generates region information including at least a representative image and a group ID (group information) by performing the processes illustrated in FIGS. 11 and 12 every time a target region is specified in the medical image displayed by the medical image browsing unit 612. Specifically, in this embodiment, the region information generation unit 614 generates medical images including indicators corresponding to target regions included in the same group specified once every time a target region is specified in the medical image as illustrated in the representative images 740 and 760 of FIG. 7.

Thereafter, the region information input unit 115 of the medical report generation apparatus 10 obtains region information (an updated representative image and a group ID) from the medical image browsing apparatus 60 through the communication unit 120 every time a target region is specified in the medical image. Then the medical report data display unit 118 of the medical report generation apparatus 10 updates and displays the representative image in the medical report such that the group is distinguishable every time the region information input unit 115 obtains region information. Specifically, in this embodiment, the region information input unit 115 obtains, as a representative image, a medical image including indicators corresponding to target regions included in the same group specified once from the medical image browsing apparatus 60 as illustrated in the representative images 740 and 760 of FIG. 7. Then, in this embodiment, the medical report data display unit 118 updates and displays the representative image including the indicators indicating the target regions included in the same group specified once every time the region information input unit 115 obtains region information.

With this configuration, by specifying a plurality of associated lesions as target regions included in the same group, the plurality of associated lesions may be recognized by only checking a representative image included in a medical report. By this, operation efficiency of a doctor who refers to the medical report may be improved.

Note that, if the same region information has been already stored when information on findings input by the medical image browsing apparatus 60 and region information are transmitted to the medical report generation apparatus 10, information on findings associated with the same region information is updated in this embodiment. However, in this case, the information on the findings may be added. In the case of the addition, display may be performed such that a plurality of information on findings is associated with one region information or the region information may be copied.

Furthermore, when the region information is displayed in the medical image browsing apparatus 60, corresponding region information and corresponding findings information in the medical report generation apparatus 10 may be highlighted. In this case, if information on a plurality of findings is associated with one region information, all the associated findings information may be highlighted.

Furthermore, when the region information is displayed in the medical image browsing apparatus 60, the findings/diagnosis input window 1012 may be simultaneously displayed. In this case, if associated findings information exists, the findings information is automatically displayed. Furthermore, the window 1012 may be displayed at a time when an image immediately before or after an image including the region information is displayed even if the region information is not displayed.

Moreover, when the region information generation unit 614 of the medical image browsing apparatus 60 generates region information, the region information is transmitted to the medical report generation apparatus 10 after findings corresponding to the region information is written in this embodiment. However, the region information may be transmitted to the medical report generation apparatus 10 immediately after the region information generation unit 614 of the medical image browsing apparatus 60 generates the region information. In this case, the region information is listed in the medical report generation apparatus 10 in an order of generation. Note that if findings information corresponding to a portion the same as that of region information exists, the findings information may be automatically associated with the region information.

Furthermore, the medical image browsing apparatus 60 may not generate region information and a unit which transmits information associated with region information may be disposed in the medical report generation apparatus 10. When an insert key is pressed in the medical image browsing apparatus 60, for example, a captured image of a screen being displayed in the medical image browsing apparatus 60 may be generated and may be transmitted to the medical report generation apparatus 10 as a representative image. In this case, an entire displayed image may be automatically set as a target region.

Furthermore, the medical image browsing apparatus 60 may subsequently transmit existing region information to the medical report generation apparatus 10. In this case, a target region displayed in the medical image browsing apparatus 60 may be specified by a mouse or the like. Furthermore, a target region may be specified in the following method. That is, a unique ID is issued for a target region and the ID is pronounced.

Moreover, findings may be written in the medical image browsing apparatus 60 without the generation of region information performed by the medical image browsing apparatus 60. In this case, the described findings may be immediately transmitted to the medical report generation apparatus 10, an icon or a title indicating that the findings has been written may be displayed in the medical image browsing apparatus 60.

Furthermore, when the region information generation unit 614 of the medical image browsing apparatus 60 generates a representative image of region information, different colors may be used for different target regions on a sliced image. In this case, different findings may be displayed in different colors corresponding to the colors of the target regions.

Moreover, although the findings/diagnosis input window 1012 is displayed for input of findings information associated with region information when the region information is generated in this embodiment, the region information and the findings information may be associated with each other in other methods. For example, the findings information and the region information may be associated with each other by selecting the region information using the medical image browsing apparatus 60 after the findings information is input using the medical report generation apparatus 10. Furthermore, the region information being displayed in the medical image browsing apparatus 60 may be automatically associated with the findings information when the findings information is input using the medical report generation apparatus 10, for example.

Although generated region information is saved as metadata of an image in this embodiment, the generated region information may be saved in other methods. The generated region information may be saved in the medical report generation apparatus 10. In this case, the region information included in the medical report generation apparatus 10 is saved in the region information storage unit 620 when the medical image browsing apparatus 60 and the medical report generation apparatus 10 are activated.

Second Embodiment

Next, a second embodiment will be described.

A schematic configuration of a medical report generation system according to the second embodiment is the same as that of the medical report generation system 100 according to the first embodiment illustrated in FIG. 1. Furthermore, a hardware configuration of a medical report generation apparatus 10 according to the second embodiment and a hardware configuration of a medical image browsing apparatus 60 according to the second embodiment are the same as that of the medical report generation apparatus 10 according to the first embodiment illustrated in FIG. 2 and that of the medical image browsing apparatus 60 according to the first embodiment, respectively. A functional configuration of the medical report generation apparatus 10 according to the second embodiment is the same as that of the medical report generation apparatus 10 according to the first embodiment illustrated in FIG. 4. A functional configuration of the medical image browsing apparatus 60 according to the second embodiment is the same as that of the medical image browsing apparatus 60 according to the first embodiment illustrated in FIG. 5. Hereinafter, descriptions of portions the same as those of the first embodiment are omitted, and portions different from the first embodiment will be described.

In the first embodiment, as illustrated in FIG. 11, when the region information generation unit 614 of the medical image browsing apparatus 60 generates region information, a group ID is automatically assigned such that target regions included in the same image are included in the same group.

In this case, the grouping of region information may be performed in other methods. For example, a unit which allows a user, such as a doctor, to manually specify a plurality of target regions and which groups region information corresponding to the plurality of regions may be provided. Alternatively, a type of a lesion may be estimated from characteristics of an image included in a region, and region information corresponding to regions including the same type of lesion may be grouped. Furthermore, an internal organ included in a region may be specified and region information corresponding to the region may be grouped for each internal organ. Moreover, region information of regions under the same display condition, such as mediastinum or a lung field, may be grouped. However, if the region information is grouped in one of the methods described above, it may be difficult to simultaneously recognize the region information in the same group in a single representative image. Therefore, the region information in the same group is distinguishable taking the display of the region information in the medical report generation apparatus 10 into consideration in the second embodiment.

In the second embodiment, in step S804 of FIG. 8, the process of grouping region information in the flowchart of FIG. 11 and the process of updating representative images in the flowchart of FIG. 12 are not performed.

Figure 13:
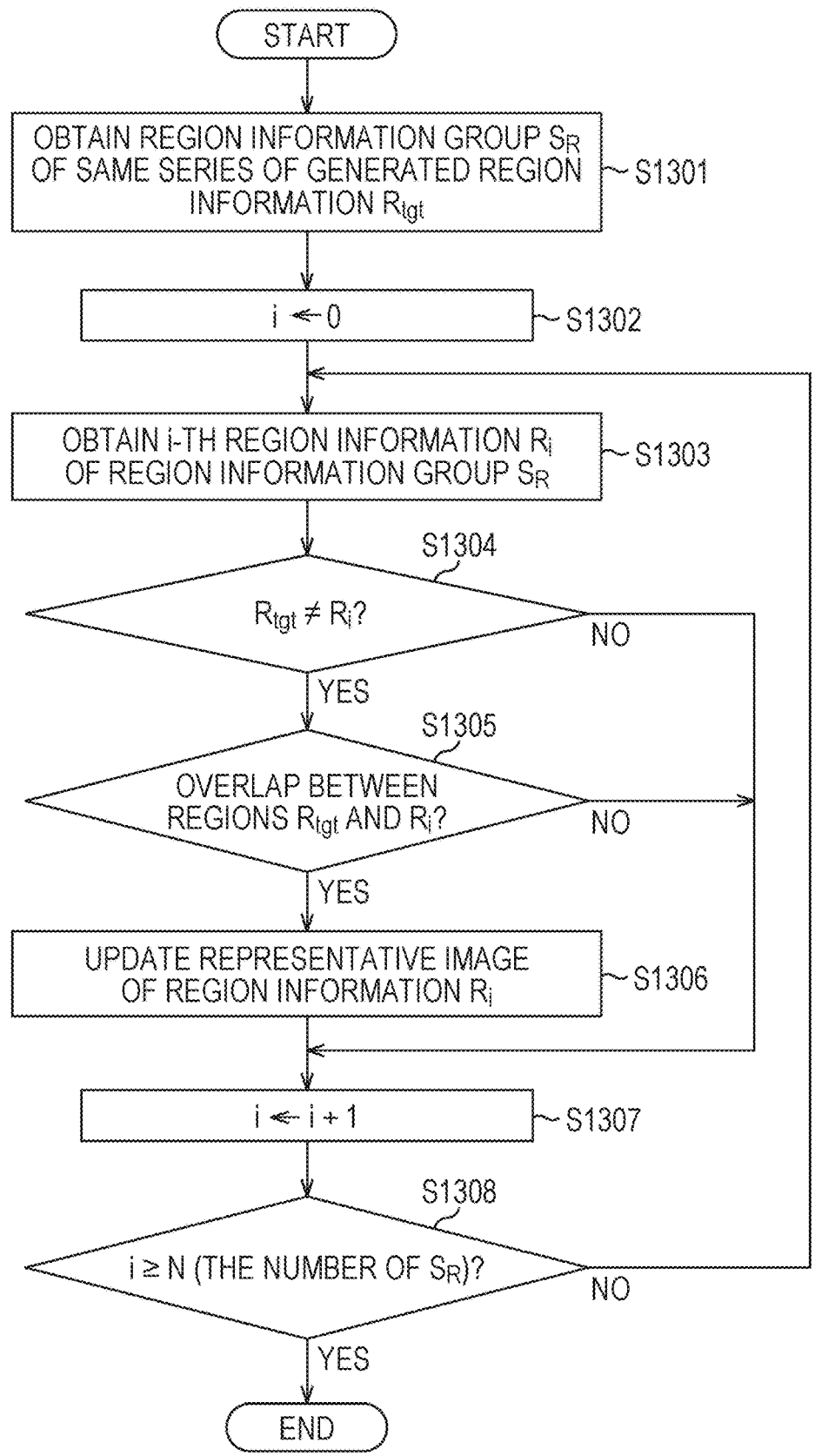
FIG. 13 is a flowchart of a procedure of a process of updating representative images of region information according to a second embodiment.

In the second embodiment, in step S804 of FIG. 8, a process of updating representative images in a flowchart of FIG. 13 is performed. Specifically, in the second embodiment, not only the grouped region information but also all representative images including generated region information are updated. In the description below, region information generated by a region information generation unit 614 is denoted by "$R_{tgt}$".

FIG. 13 is a flowchart of a procedure of a process of updating representative images of region information according to the second embodiment.

In step S1301, the region information generation unit 614 of the medical image browsing apparatus 60 obtains a region information group $S_R$ which is the same series as the region information $R_{tgt}$ among region information stored in the region information storage unit 620. It is assumed here that the number of region information included in the region information group $S_R$ is N.

In step S1302, the region information generation unit 614 of the medical image browsing apparatus 60 assigns 0 to a variable i indicating region information to be processed included in the region information group $S_R$.

In step S1303, the region information generation unit 614 of the medical image browsing apparatus 60 obtains i-th region information $R_i$ in the region information group $S_R$.

In step S1304, the region information generation unit 614 of the medical image browsing apparatus 60 determines whether the region information $R_{tgt}$ is different from the region information $R_i$. The difference determination of the region information is made by comparing region IDs with each other.

When the determination is affirmative in step S1304 (S1304: Yes), the process proceeds to step S1305.

In step S1305, the region information generation unit 614 of the medical image browsing apparatus 60 determines whether a region corresponding to the region information $R_{tgt}$ overlaps with a region corresponding to the region information $R_i$. Specifically, it is determined whether the region corresponding to the region information $R_{tgt}$ overlaps with a sliced image which includes the region corresponding to the region information $R_i$. If the regions are represented in a three dimensional manner, the determination is made in the three dimensional manner.

When the determination is affirmative in step S1305 (S1305: Yes), the process proceeds to step S1306.

In step S1306, first, the region information generation unit 614 of the medical image browsing apparatus 60 determines that the region information $R_{tgt}$ and the region information $R_i$ are in the same group. Specifically, the same value is input to group IDs. Furthermore, the region information generation unit 614 of the medical image browsing apparatus 60 applies image processing information of the region information $R_i$ to the sliced image including the region information $R_i$, captures an image in which a region corresponding to the region information $R_i$ is in a selection state (a display state), and updates and stores the image as a representative image of the region information $R_i$. It is assumed here that the sliced image which is a source of the capturing includes, in addition to an indicator indicating the region corresponding to the region information $R_i$, an indicator indicating the region corresponding to other region information including the region information $R_{tgt}$. Furthermore, all the steps of the process are performed in the background and are not displayed in a screen of the medical image browsing apparatus 60.

When the process in step S1306 is terminated, when the determination is negative in step S1304 (S1304: No), or when the determination is negative in step S1305 (S1305: No), the process proceeds to step S1307.

In step S1307, the region information generation unit 614 of the medical image browsing apparatus 60 adds 1 to the variable i.

In step S1308, the region information generation unit 614 of the medical image browsing apparatus 60 determines whether the variable i is equal to or larger than N which is the number of region information included in the region information group $S_R$. When the determination is negative in step S1308 (S1308: No), the process returns to step S1303 and the process in step S1303 onwards is performed again.

On the other hand, when the determination is affirmative in step S1308 (S1308: Yes), the process of the flowchart of FIG. 13 is terminated.

Figure 14A:
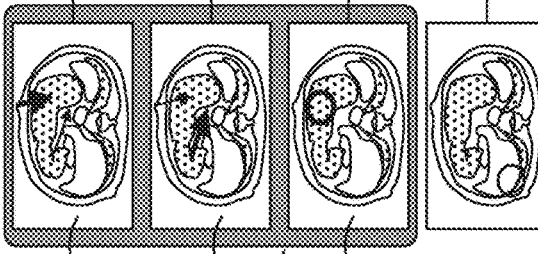

FIGS. 14A and 14B are diagrams illustrating GUI screens displayed in the medical report generation apparatus 10 according to the second embodiment.

In a GUI screen 1410 of FIG. 14A, representative images 1411 to 1413 in region information in the same group (that is, having the same group ID) are surrounded by a frame line 1414 in display. In this way, the group of the region information is clarified.

In a GUI screen 1420 of FIG. 14B, the representative images 1411 to 1413 in the region information in the same group (that is, having the same group ID) are associated with a common findings input frame 1421 and a common diagnosis input frame 1422 in display. In this way, the group of the region information is clarified.

Note that the grouping according to region information illustrated in FIGS. 14A and 14B may be manually performed using the medical report generation apparatus 10.

According to the second embodiment, as with the first embodiment, by specifying a plurality of associated lesions as target regions included in the same group, the plurality of associated lesions may be recognized only by checking representative images (a plurality of representative images) included in a medical report. By this, operation efficiency of a doctor who refers to the medical report may be improved.

Third Embodiment

Next, a third embodiment will be described. In a description of the third embodiment below, only portions different from the first and second embodiments will be described.

In the foregoing first and second embodiments, it is assumed that the region information generation unit 614 of the medical image browsing apparatus 60 reflects all indicators indicating target regions included in the same medical image on a representative image when the representative image is updated. However, the present invention is not limited to the first, second, and third embodiments.

Figure 15:
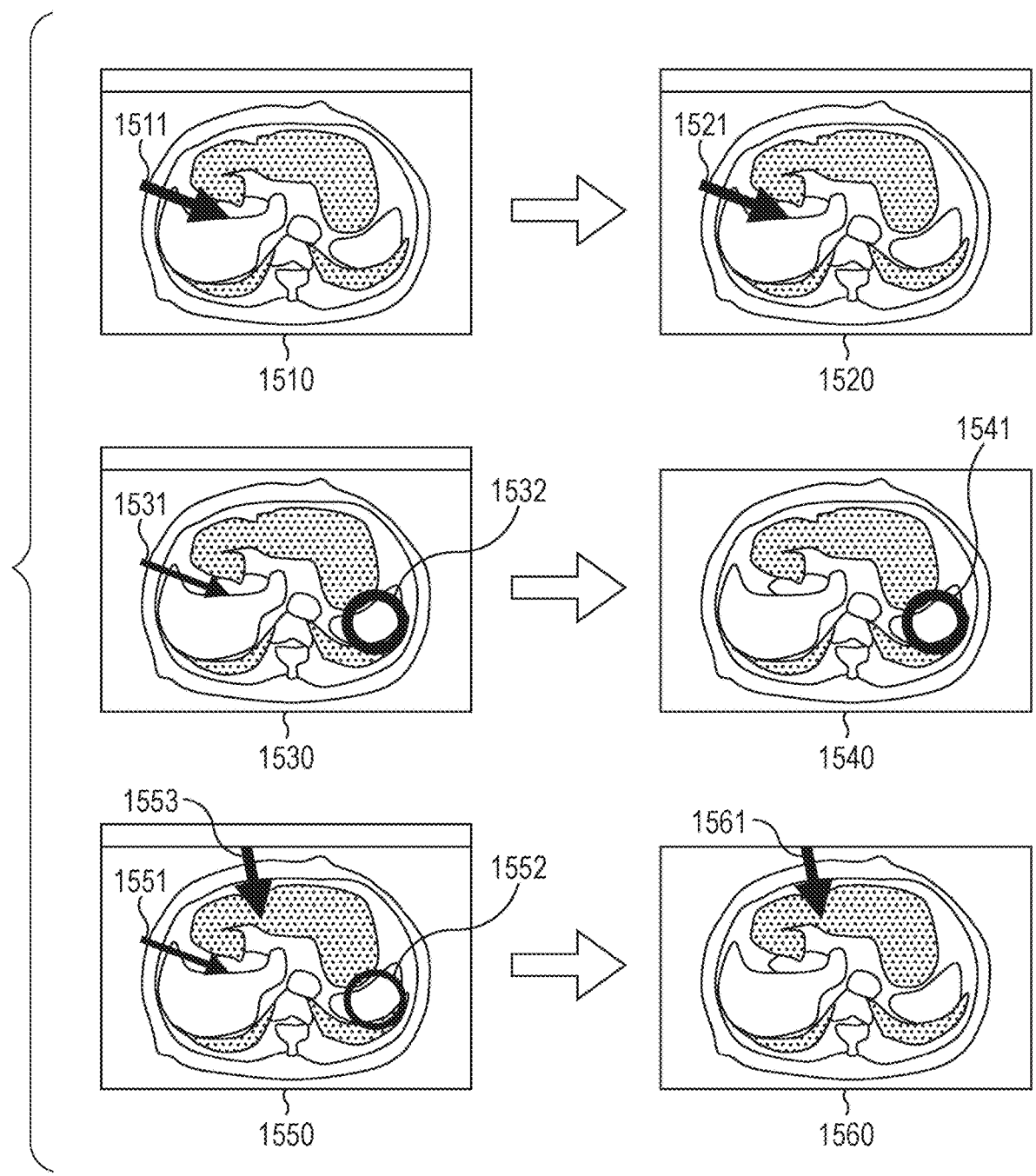
FIG. 15 is a diagram illustrating representative images included in region information according to a third embodiment.

FIG. 15 is a diagram illustrating representative images included in region information according to the third embodiment.

On a left side in FIG. 15, medical images 1510, 1530, and 1550 displayed in an output device 15 of a medical image browsing apparatus 60 are illustrated. Furthermore, in FIG. 15, the medical images 1510, 1530, and 1550 are displayed in the output device 15 in this order as time proceeds. The medical image 1510 includes an indicator 1511 indicating a target region specified by a doctor through an input device 14. The medical image 1530 includes, in addition to an indicator 1531 based on the indicator 1511 in the medical image 1510, an indicator 1532 indicating a target region specified next by the doctor through the input device 14. In this case, a display state of the indicator 1532 is different from that of the indicator 1531. Furthermore, in the example of FIG. 15, the indicator 1532 is thickly indicated so as to clarify the region specified at this time point and the indicator 1531 is thinly indicated (thinner than the indicator 1511). The medical image 1550 includes, in addition to an indicator 1551 based on the indicator 1531 in the medical image 1530 and an indicator 1552 based on the indicator 1532 in the medical image 1530, an indicator 1553 indicating a target region specified next by the doctor through the input device 14. In this case, a display state of the indicator 1553 is different from those of the indicators 1551 and 1552. Furthermore, in the example of FIG. 15, the indicator 1553 is thickly indicated so as to clarify the region specified at this time point and the indicators 1551 and 1552 are thinly indicated. It is assumed here that the medical images 1510, 1530, and 1550 have the same content and only the indicators included in the medical images 1510, 1530, and 1550 are different from one another in this embodiment. Furthermore, in this embodiment, the target regions specified in the individual medical images 1510, 1530, and 1550 are specified by the doctor as a plurality of associated lesion regions.

On a right side in FIG. 15, representative images 1520, 1540, and 1560 generated by a region information generation unit 614 are illustrated. The representative image 1520 is captured when region information thereof is generated (when the medical image 1510 is displayed in a medical image browsing apparatus 60 in the example of FIG. 15). An indicator 1521 based on the indicator 1511 in the medical image 1510 is included in the representative image 1520. Specifically, the indicator 1521 based on the indicator 1511 indicating a target region specified in the medical image 1510 is included in the representative image 1520. The representative image 1540 is captured when region information thereof is generated (when the medical image 1530 is displayed in the medical image browsing apparatus 60 in the example of FIG. 15). However, the representative image 1540 does not include an indicator based on the indicator 1531 included in the medical image 1530, but only includes an indicator 1541 based on the indicator 1532 included in the medical image 1530. Specifically, only the indicator 1541 based on the indicator 1532 indicating a target region specified in the medical image 1530 (a target region specified at a time of the specifying) is included in the representative image 1540. The representative image 1560 is captured when the region information is generated (when the medical image 1550 is displayed in the medical image browsing apparatus 60 in the example of FIG. 15). However, the representative image 1560 does not include an indicator based on the indicator 1551 included in the medical image 1550 and an indicator based on the indicator 1552 included in the medical image 1550, but only includes an indicator 1561 based on the indicator 1553 included in the representative image 1550. Specifically, only the indicator 1561 based on the indicator 1553 indicating a target region specified in the medical image 1550 (a target region specified at a time of the specifying) is included in the representative image 1560.

Since the representative image is updated as illustrated in FIG. 15, the relationship between the region information and the representative image may be easily recognized. Furthermore, also in the third embodiment, since representative images corresponding to region information in the same group are distinguishable as illustrated in FIGS. 14A and 14B, the associated region information may be recognized only by checking a medical report generated by a medical report generation apparatus 10.

In the third embodiment, every time the region information generation unit 614 of the medical image browsing apparatus 60 specifies a target region in a medical image displayed by the medical image browsing unit 612, region information at least including a representative image and a group ID (group information) is generated. Specifically, in this embodiment, every time a target region is specified in a medical image, the region information generation unit 614 generates, as a representative image, a medical image including an indicator corresponding to a target region specified at the time of the specifying as illustrated in the representative images 1540 and 1560 of FIG. 15. In this case, the region information generation unit 614 generates information for distinguishing a certain group from other groups as a group ID (group information).

Thereafter, a region information input unit 115 of the medical report generation apparatus 10 obtains the region information (the updated representative image and the group ID) from the medical image browsing apparatus 60 through a communication unit 120 every time a target region is specified in the medical image. Then a medical report data display unit 118 of the medical report generation apparatus 10 updates and displays the representative image in the medical report such that the group is distinguishable every time the region information input unit 115 obtains region information. Specifically, in this embodiment, the region information input unit 115 obtains, as a representative image, a medical image including an indicator corresponding to a target region specified at a time of the specifying from the medical image browsing apparatus 60 as illustrated in the representative images 1540 and 1560 of FIG. 15. Then, in this embodiment, the medical report data display unit 118 updates and displays a plurality of representative images including indicators indicating target regions included in the same group as the same group in accordance with a group ID (group information) every time the region information input unit 115 obtains region information. In this case, the medical report data display unit 118 displays the plurality of representative images 1411 to 1413 included in the same group as illustrated in FIGS. 14A and 14B so that the group is distinguishable.

With this configuration, by specifying a plurality of associated lesions as target regions included in the same group, the plurality of associated lesions may be recognized only by checking representative images included in a medical report. By this, operation efficiency of a doctor who refers to the medical report may be improved.

Other Embodiments

According to the foregoing first to third embodiments, the region information grouping process and the process of updating representative images corresponding to region information in the same group are performed by the medical image browsing apparatus 60 (that is, the region information generation unit 614). However, the present invention is not limited to this, and a case where the region information grouping process and the process of updating representative images corresponding to region information in the same group are executed by the medical report generation apparatus 10 (for example, the region information input unit 115) is also included in the present invention.

In this case, a representative image is not stored in the region information storage unit 620 as a portion of region information but a representative image may be stored in a medical report data storage unit 121 as a portion of the medical report data. However, a region ID of the representative image is recognized even after the storage.

Note that the foregoing embodiments of the present invention are merely concrete examples for embodying the present invention, and the technical scope of the present invention is not limited by them. Specifically, various modifications of the present invention may be made without departing from the technical scope and the main features of the present invention.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-080539 filed Apr. 13, 2016, which is hereby incorporated by reference herein in its entirety.

What is claimed is:

1. An apparatus comprising:
   one or more processors and a memory coupled to each other and cooperating to act as:
   a receiving unit configured to receive a designation for a first target region in a medical image;
   a generation unit configured to generate a first representative image showing a first indicator by capturing a medical image showing the first indicator, wherein the first indicator represents the first target region; and
   a display control unit configured to display a first medical report including the first representative image showing the first indicator and first findings for the first target region, wherein the receiving unit receives a designation for a second target region different from the first target region in the medical image, wherein the generation unit generates a second representative image showing the first indicator and a second indicator by capturing a medical image showing the first indicator and the second indicator, wherein the second indicator represents the second target region, and the generation unit updates the first representative image by adding the second indicator to the first representative image showing the first indicator, wherein the display control unit displays the first medical report including the first findings and the updated first representative image showing the first indicator and the second indicator, and a second medical report including second findings and the second representative image showing the first indicator and the second indicator, and wherein the second indicator in the second representative image is emphasized.

2. The apparatus according to claim 1, wherein the generation unit generates group information indicating the first indicator and the second indicator.

3. The apparatus according to claim 2, wherein the display control unit displays the first representative image of the first medical report and the second representative image of the second medical report in accordance with the group information.

4. The apparatus according to claim 1, wherein the first indicator and the second indicator are included in the same plane of the medical image.

5. The apparatus according to claim 1, wherein the first representative image is an image in which the first indicator and the second indicator are distinguishable.

6. The apparatus according to claim 1, wherein the second target region includes at least one target region.

7. The apparatus according to claim 1, wherein the first indicator and the second indicator has have a unique appearance in the first representative image and the second representative image.

8. The apparatus according to claim 1, wherein the first indicator and the second indicator in the first representative image and the second representative image indicate a same lesion.

9. The apparatus according to claim 1, wherein the first indicator and the second indicator in the first representative image and the second representative image indicate a same internal organ.

10. The apparatus according to claim 1, wherein the medical image includes a plurality of sliced images, and
wherein the first representative image and the second representative image are sliced images.

11. The apparatus according to claim 1, wherein the display control unit displays the first representative image of the first medical report and the second representative image of the second medical report such that a group is distinguishable.

12. A method for controlling an apparatus, the method comprising:
receiving a designation for a first target region in a medical image;
generating a first representative image showing a first indicator by capturing a medical image showing the first indicator, wherein the first indicator represents the first target region; and
displaying a first medical report including the first representative image showing the first indicator and first findings for the first target region;
receiving a designation for a second target region different from the first target region in the medical image;
generating a second representative image showing the first indicator and a second indicator by capturing a medical image showing the first indicator and the second indicator, wherein the second indicator represents the second target region, and updating the first representative image by adding the second indicator to the first representative image showing the first indicator; and
displaying the first medical report including the first findings and the updated first representative image showing the first indicator and the second indicator, and the second medical report including second findings and the second representative image showing the first indicator and the second indicator,
wherein the second indicator in the second representative image is emphasized.

13. A non-transitory computer readable medium storing a program for causing a one or more processors to execute the method according to claim 12.

14. A system comprising:
one or more processors and a memory coupled to each other and cooperating to act as:
a receiving unit configured to receive a designation for a first target region in a medical image;
a generation unit configured to generate a first representative image showing a first indicator by capturing a medical image showing the first indicator, wherein the first indicator represents the first target region; and
a display control unit configured to display a first medical report including the first representative image showing the first indicator and first findings for the first target region,
wherein the receiving unit receives a designation for a second target region different from the first target region in the medical image,
wherein the generation unit generates a second representative image showing the first indicator and a second indicator by capturing a medical image showing the first indicator and the second indicator, wherein the second indicator represents the second target region, and the generation unit updates the first representative image by adding the second indicator to the first representative image showing the first indicator,
wherein the display control unit displays the first medical report including the first findings and the updated first representative image showing the first indicator and the second indicator, and the second medical report including second findings and the second representative image showing the first indicator and the second indicator, and
wherein the second indicator in the second representative image is emphasized.

* * * * *